(12) United States Patent
Husher

(10) Patent No.: US 7,207,939 B2
(45) Date of Patent: Apr. 24, 2007

(54) APPARATUS AND METHOD FOR ANALYZING A LIQUID IN A CAPILLARY TUBE OF A HEMATOLOGY INSTRUMENT

(75) Inventor: Frederick K. Husher, Pembroke Pines, FL (US)

(73) Assignee: Coulter International Corp., Miami, FL (US)

( * ) Notice: Subject to any disclaimer, the term of this patent is extended or adjusted under 35 U.S.C. 154(b) by 320 days.

(21) Appl. No.: 10/264,077

(22) Filed: Oct. 3, 2002

(65) Prior Publication Data

US 2004/0065143 A1    Apr. 8, 2004

(51) Int. Cl.
*A61B 5/00* (2006.01)
*A61B 8/00* (2006.01)

(52) U.S. Cl. ............... 600/370; 600/438; 422/73

(58) Field of Classification Search ........ 600/370–372, 600/437–438; 436/70, 73–74; 422/44, 73, 422/99–102
See application file for complete search history.

(56) References Cited

U.S. PATENT DOCUMENTS

| | | | |
|---|---|---|---|
| 3,292,093 A | 12/1966 | Clarke et al. | |
| 3,720,097 A * | 3/1973 | Kron | 73/54.04 |
| 3,848,796 A | 11/1974 | Bull | |
| 4,432,231 A * | 2/1984 | Napp et al. | 73/290 V |
| 4,441,358 A * | 4/1984 | Osborne | 73/54.07 |
| 4,485,821 A | 12/1984 | Iinuma | |
| 4,554,821 A * | 11/1985 | Kiesewetter et al. | 73/54.07 |
| 4,572,664 A | 2/1986 | Hanson | |
| 5,073,719 A | 12/1991 | Ricci | |
| 5,209,903 A | 5/1993 | Kanamori et al. | |
| 5,409,010 A | 4/1995 | Beach et al. | |
| 5,650,332 A | 7/1997 | Gao et al. | |
| 5,804,145 A | 9/1998 | Gao et al. | |
| 5,827,746 A | 10/1998 | Duic | |
| 5,853,994 A * | 12/1998 | Gopinathan et al. | 435/6 |
| 5,895,760 A | 4/1999 | Chen et al. | |
| 6,402,703 B1* | 6/2002 | Kensey et al. | 600/573 |
| 6,542,761 B1* | 4/2003 | Jahn et al. | 600/310 |
| 6,740,036 B1* | 5/2004 | Lee et al. | 600/437 |
| 6,751,490 B2* | 6/2004 | Esenaliev et al. | 600/310 |
| 6,854,338 B2* | 2/2005 | Khuri-Yakub et al. | 73/861.27 |
| 2004/0054283 A1* | 3/2004 | Corey et al. | 600/438 |

FOREIGN PATENT DOCUMENTS

WO    WO98/02726    1/1998

OTHER PUBLICATIONS

Bull, et al, "The Zeta Sedimentation Ratio", *Blood*, vol. 40, pp. 550-559, Oct. 1972.

(Continued)

*Primary Examiner*—Francis J. Jaworski
(74) *Attorney, Agent, or Firm*—Howson and Howson; Mitchell E. Alter

(57) ABSTRACT

An apparatus and method for determining the density and fluid-type of a fluid flowing in a capillary tube, the velocity and viscosity of a blood sample flowing in a capillary tube, the erythrocyte sedimentation rate (ESR) of a blood sample after flow has been brought to an abrupt stop in a capillary tube, and/or the zeta sedimentation rate (ZSR) of a blood sample after flow has been brought to an abrupt stop in a capillary tube. These measurements are accomplished by directing a waveform pulse, such as an ultrasound pulse, at a pre-determined frequency transversely across the capillary tube and sample fluid, and by determining the flight of time of the pulse through the capillary tube and sample fluid and/or the Doppler shift of the echo signals reflecting off cells moving forwardly or transversely within a flowing, or stationary, blood sample.

35 Claims, 10 Drawing Sheets

OTHER PUBLICATIONS

Ralph Talkers, "Erythrocyte Sedimentation Rate/Zeta Sedimentation Rate", *Emer. Med. Clin. Of North America*, vol. 4, pp. 87-93, Feb. 1986.

Stonebridge, et al., "Spiral laminar flow in arteries?", *The Lancet*, V338(8779), pp. 1360-1361, Nov. 30, 1991.

Moseley, et al., "A Comparison of the Wintrobe, the Westergren and the ZSR erythrocyte sedimentation rate (ESR) methods to a candidate reference method", *Clin. Lab. Haemat.*, vol. 4, pp. 169-178, 1982.

* cited by examiner

APPARATUS AND METHOD FOR ANALYZING A LIQUID IN A CAPILLARY TUBE OF A HEMATOLOGY INSTRUMENT

FIELD OF THE INVENTION

The present invention relates to an apparatus and method for analyzing a blood sample in vitro, and more particularly, the present invention relates to a hematology instrument, sensor, or the like, and method which are utilized to analyze blood samples and/or are associated with the generation of blood smear slides and which are capable of determining one or more of the density/fluid-type of the sample, the viscosity of the sample, and the erythrocyte sedimentation rate (ESR) and zeta sedimentation rate (ZSR) of the sample.

BACKGROUND OF THE INVENTION

An apparatus for analyzing blood samples in vitro typically requires fluids to be passed through a capillary tube in a predefined sequence, such as, air, isotonic fluids (ie., salt water), blood, isotonic fluids and then air. The apparatus typically includes one or more fluid-type detectors for determining the presence, or lack thereof, of blood within the capillary tube at various locations along the length of the tube within the instrument. Conventionally, the detection process is accomplished with an optical density measurement in which light of a known intensity is transmitted through the capillary tube and received and measured to determine the intensity of the light passing through the tube and to enable a determination of the density of the fluid within the tube. Since air and isotonic fluids are substantially clear in comparison to a blood sample, the presence of blood, as well as the leading and trailing edges of the blood sample within the sequence of fluids, is detected and identified by the optical density measurement.

Some blood processing apparatus are associated with an automated mechanism for generating blood smears on microscope slides. Such apparatus should measure, estimate, be supplied with, or otherwise determine the viscosity of a blood sample to determine smear hold time, velocity, and acceleration of a smear wedge component needed to create an optimal blood smear on the slide. Examples of automated slide making apparatus, smear wedge components, and related methods are disclosed in U.S. Pat. Nos. 5,650,332 and 5,804,145 issued to Gao et al. and U.S. Pat. No. 5,209,903 issued to Kanamori et al.

The movement of a blood-smearing member across the slide according to the Gao patents is controlled as a function of various predetermined physical parameters of the blood identified from blood analysis data. For instance, the primary parameter for determining smear wedge velocity is hematocrit HCT, although other hematology parameters are utilized to add or subtract to the velocity to correct for abnormal cases and/or for the presence of drugs. The Kanamori patent utilizes a pair of optical sensors and a timer to determine the amount of time required for a leading edge of the blood sample to pass from a first sensor to a second sensor located downstream thereof. The elapsed time measurement is utilized to determine the viscosity of the sample.

Some blood processing apparatus permit the erythrocyte sedimentation rate (ESR) and/or the zeta sedimentation rate (ZSR) of a blood sample to be determined. The ESR is a measure of the degree of settling of erythrocytes in plasma within an anticoagulated whole blood specimen during a period of time. The basic ESR measurement is the rate at which the turbid corpuscular part of the blood sample consisting of red and white blood cells and platelets separates from the nearly clear fluid plasma or serum. An elevated ESR is believed to be caused by an increase in the acute-phase asymmetrical proteins of plasma, largely fibrinogen, $\alpha_2$ globulin and $\gamma$globulin and is believed to indicate the presence of inflammation of the patient.

The ZSR is a measure of the packing of erythrocytes under a standardized stress (zetacrit). Integral proteins on red cell membranes contain sialic acid that provides erythrocytes with a negative charge. This negativity between cells, known as the so-called zeta potential, causes cells to repel one another as they move through the circulation system of the body. Altered plasma proteins, such as fibrinogen and globulins, in the surrounding medium, can cause a decrease in zeta potential. A decrease in zeta potential causes an increase in ESR. Thus, the ZSR measurement, expressed in % as the red cell hematocrit, assesses the ease with which the red blood cells pack under stress and is presumably related to the zeta potential of red blood cells when suspended in a particular plasma. A normal ZSR value for both males and females is in a range of 40% to 50% and is unaffected by anemia.

A method known as the Westergren method has been recommended by the International Council (formerly, Committee) for Standardization in Haematology as the method of choice for measuring ESR. This method has been utilized since the 1920s and is described in *Br. J. Haematol.*, 24:671–673, 1973. Also see the following published references: Talkers, "Erythrocyte Sedimentation Rate/Zeta Sedimentation Rate", Emer. Med. Clin. Of North America, Vol. 4, pp 87–93, February 1986; Moseley et al., "A Comparison of the Wintrobe, The Westergren and the ZSR Erthrocyte Sedimentation Rate (ESR) Methods to a Candidate Reference Method", Clin Lab Haemat., Vol. 4, pp 169–178, 1982; and Bull et al., "The Zeta Sedimentation Ratio", Blood, Vol. 40, pp 550–559, October 1972. The Westergren method is a gravity-based method in which a volume of blood is placed in a vertically oriented tube and in which the rate of sedimentation of the cells within the tube is recorded at fixed intervals over a period of time typically greater than an hour.

More recent examples of apparatus and methods for measuring sedimentation rates are disclosed by U.S. Pat. No. 3,848,796 issued to Bull and U.S. Pat. No. 5,827,746 issued to Duic. The Bull patent discloses a centrifuge apparatus, known as the so-called Zetafuge, that measures ZSR by applying a controlled centrifugation to a blood sample producing alternating compaction and dispersion of erythrocytes and by measuring how closely the erythrocytes approach one another under a specific standardized artificial gravitational force.

The Duic patent discloses an apparatus for measuring ESR in which a blood sample is preheated to an elevated temperature to minimize the viscosity of the sample and is then passed through a thin tube at a constant velocity in a manner that causes the cells to be densely packed within the center of the thin tube. Thereafter, the preheated blood sample is abruptly stopped thereby causing the plasma to stop. However, the kinetic energy and zeta potential of the cells cause the cells to continue moving forward and away from the center of the tube. A focused optical density measurement is performed through the center of the tube and an ESR measurement is obtained by recording a drop in optical attenuation based on the rate at which the cells move away from the center of the tube over a 30-second interval. This rate of particle movement within the sample is then extrapolated to the conventional gravity-based separation Westergren measurement.

Although the aforementioned apparatus, methods, systems and techniques may function satisfactorily for their intended purposes, the use of optical density measurements has some disadvantages and significant limitations. An optical density measurement can provide information only based on the average behavior of the fluid in the tube independent of cell velocities. An optical density measurement cannot be utilized to isolate the behavior of any one cross sectional position within a tube. For example, the optical density measurement cannot determine the peak velocity at the center of the tube nor can it differentiate the fluid velocity at the center of the tube relative to the fluid velocity at the edges of the tube. In addition, optical density sensors are only useful when used in combination with tubing have a small inner diameter that permits a sufficient amount of light to pass through the tubing and sample. Of course, use of small inner diameter tubing limits the fluid handling flow rate of samples through the hematology instrument.

The presence of microbubbles within a blood sample also presents a significant challenge since the presence of microbubbles are unrecognizable by optical density sensors and greatly effects the value of the optical density measurement. Further, optical density sensors must remain stationary relative to the tube through which the sensors obtain an optical density measurement for the sensors to remain properly calibrated. Any inadvertent movement of the tube relative to the sensors will require a time consuming recalibration of the sensors. Such inadvertent movement often occurs during the course of troubleshooting the blood-processing instrument for non-sensor related reasons.

A problem with generating blood smears is that hematology parametric data of blood samples lose value over time. Thus, a smear should be generated as quickly as possible after blood analysis and/or viscosity measurements to ensure that an optimal slide is created. Similarly, the measurement of ESR and ZSR typically require a significant initial dead time which has a significant effect on the time required for analysis. Such analysis, therefore, cannot readily be accomplished in succession with other analyses that can be performed much quicker, such as, for instance blood cell counts.

The ESR measurement method and apparatus according to U.S. Pat. No. 5,827,746 issued to Duic also has disadvantages due to its reliance on optical density measurements. An ESR measurement is dependent on the temperature and viscosity of the sample, the protein concentration in the plasma, the erythrocyte size bias, and lipids. Lipids cause problems related to carryover and baseline drift of the optical density measurement. When a fluid column is brought to a stop, lipids will electrostatically be attracted to walls of the tubing and will continue to build-up on the walls. Platelets can also become attached to the tubing walls. The build-up causes an increase in optical attenuation of the tube and therefore, affects the optical density measurement. Thus, there is an unknown progressive error build-up that distorts the optical density and ESR measurements of all samples processed sequentially through the apparatus. The optical density measurement is also effected when a portion of the build-up is torn loose from the walls of the tube and flows within the blood sample being analyzed. Another limitation of the above stated method is that it requires an additional time-consuming process step of preheating the blood sample to a precise elevated temperature before the test can be started.

Abnormal blood samples (ie., samples with elevated ESR which are most important to identify) often have extreme blood cell counts and plasma viscosity that cause the cells to dissipate more slowly in the fluid column. Blood samples may alternatively have a low viscosity and low cell count resulting in the cells dissipating at a faster than normal rate. Neither of these conditions can be recognized, determined and/or corrected for when an optical density measurement provides the mechanism for measuring ESR.

With the foregoing in mind, a primary object of the present invention is to provide an improved apparatus and method for analyzing a liquid located in a capillary tube of a hematology instrument.

Another object of the present invention is to provide an apparatus and method that can accurately, readily and quickly determine the density of a liquid contained in a tube of a hematology instrument and whether or not microbubbles are present within the liquid.

A further object of the present invention is to provide an apparatus and method that can accurately, readily and quickly determine the velocity of individual cells within a blood sample flowing through a capillary tube and the viscosity of the blood sample.

A still further object of the present invention is to provide an apparatus and method that can accurately, readily and quickly determine the ESR and ZSR of a blood sample.

Yet another object of the present invention is to provide apparatus that is capable of use in daily operations in a cost efficient manner at relatively high fluid handling flow rates requiring only a minimum of skill to operate, utilize and maintain.

SUMMARY OF THE INVENTION

According to one aspect of the present invention, a device for analyzing a fluid sample, such as a blood sample, is provided. The device includes a capillary tube and a sensor assembly mounted thereabout. The capillary tube defines a path of travel for the flow of the blood sample in vitro, and the sensor assembly has at least one sensor for emitting a waveform pulse of a known frequency into the capillary tube transversely across the path of travel and for receiving the pulse after the pulse either propagates through the capillary tube and path of travel or is reflected from a particle, such as a cell, within the fluid. The flight of time and/or the Doppler shift of the received pulses are determined to obtain desired information concerning the fluid sample.

Fluid density is determined as a function of the flight of time of a pulse propagating at least one full trip through the tube and fluid sample. To this end, the device of the present invention has a sensor oriented perpendicular to the path of travel of the fluid sample within the capillary tube at a location where the pulse is launched into the capillary tube, or at a diametrically opposite location relative to the capillary tube, to receive the pulse.

Velocity of cell movement within a flowing, or stationary, blood sample is determined as a function of the Doppler shift of an echo signal that reflects from a cell moving within the blood sample in the capillary tube. To this end, the device of the present invention includes a sensor for receiving echo signals. The sensor can be located forward along the path of travel relative to where the pulse is launched into the capillary tube and be canted at an angle to the direction in which the ultrasound pulse is emitted into the capillary tube. Such a canted sensor is utilized to measure the velocity of forward cell movement in the capillary tube. Alternatively, or in addition thereto, the device according to the present invention can have a sensor oriented perpendicular to the capillary tube corresponding to the cross section of the tube in which the pulse is launched to detect the velocity of cells moving in a transverse direction relative to the path of travel.

Preferably, the waveform pulse is an ultrasound pulse at a preselected frequency. In addition, preferably the sensor, or sensors, are piezo crystal transducers, the capillary tube defines a straight path of travel adjacent the sensor to ensure a laminar blood sample flow, and the ultrasound pulse is emitted in a direction substantially perpendicular to the path of travel and along a diameter of the capillary tube. Further, the device according to the present invention can be utilized to determine one or more of the fluid-type of the fluid flowing within the capillary tube, the viscosity of a blood sample flowing within the capillary tube, and the erythrocyte sedimentation rate (ESR) and zeta sedimentation rate (ZSR) of a blood sample after the flow of the blood sample within the capillary tube is abruptly halted.

According to another aspect of the present invention, a method of analyzing a fluid sample, such as a blood sample, is provided. The method includes flowing a fluid sample, such as a blood sample in vitro, in a path of travel within a capillary tube and emitting a waveform pulse at a preselected frequency into the capillary tube transversely into the path of travel. The pulse is received by a sensor after the pulse propagates at least one full trip through the capillary tube and path of travel or after the pulse reflects from a particle, such as a cell, within the fluid sample. The method also includes the step of measuring the flight time of the received pulse through the tube and fluid sample, or measuring the Doppler shift of the received pulse that reflects from a cell or like particle.

According to one method of the present invention, the flighttime of the pulse through the capillary tube and fluid sample is measured to determine the density of the fluid sample. This, in turn, is utilized to determine and report the fluid-type of the fluid sample and whether or not microbubbles are present within the fluid sample. According to another method of the present invention, the Doppler shift of echo signals received from the pulse reflecting from cells moving forwardly along the path of travel in a flowing blood sample is determined to detect the velocity of blood sample movement within the capillary tube. The velocity measurement of the blood sample combined with information concerning the density of the blood sample is utilized to determine the viscosity of the blood sample.

According to yet another method of the present invention, the flow of a blood sample in the capillary tube is abruptly halted. Thereafter, the Doppler shift of echo signals created by the pulse reflecting from cells still moving in the stationary blood sample are repeatedly measured to determine the rate of decay of velocity of forward moving cells and the rate of decay of velocity of cells moving in a transverse direction. The measured rate of decay of the velocity of forward moving cells is utilized to determine an ESR value for the blood sample and the measured rate of decay of velocity of the cells moving transversely is utilized to determine a ZSR value for the blood sample.

For all these methods, preferably the waveform pulse is an ultrasound pulse that is directed substantially perpendicular to the path of travel of the fluid sample and along a diameter of the capillary tube.

BRIEF DESCRIPTION OF THE DRAWINGS

The foregoing and other objects, features and advantages of the present invention should become apparent from the following description when taken in conjunction with the accompanying drawing, in which.

DETAILED DESCRIPTION OF THE PREFERRED EMBODIMENT

Figure 1:
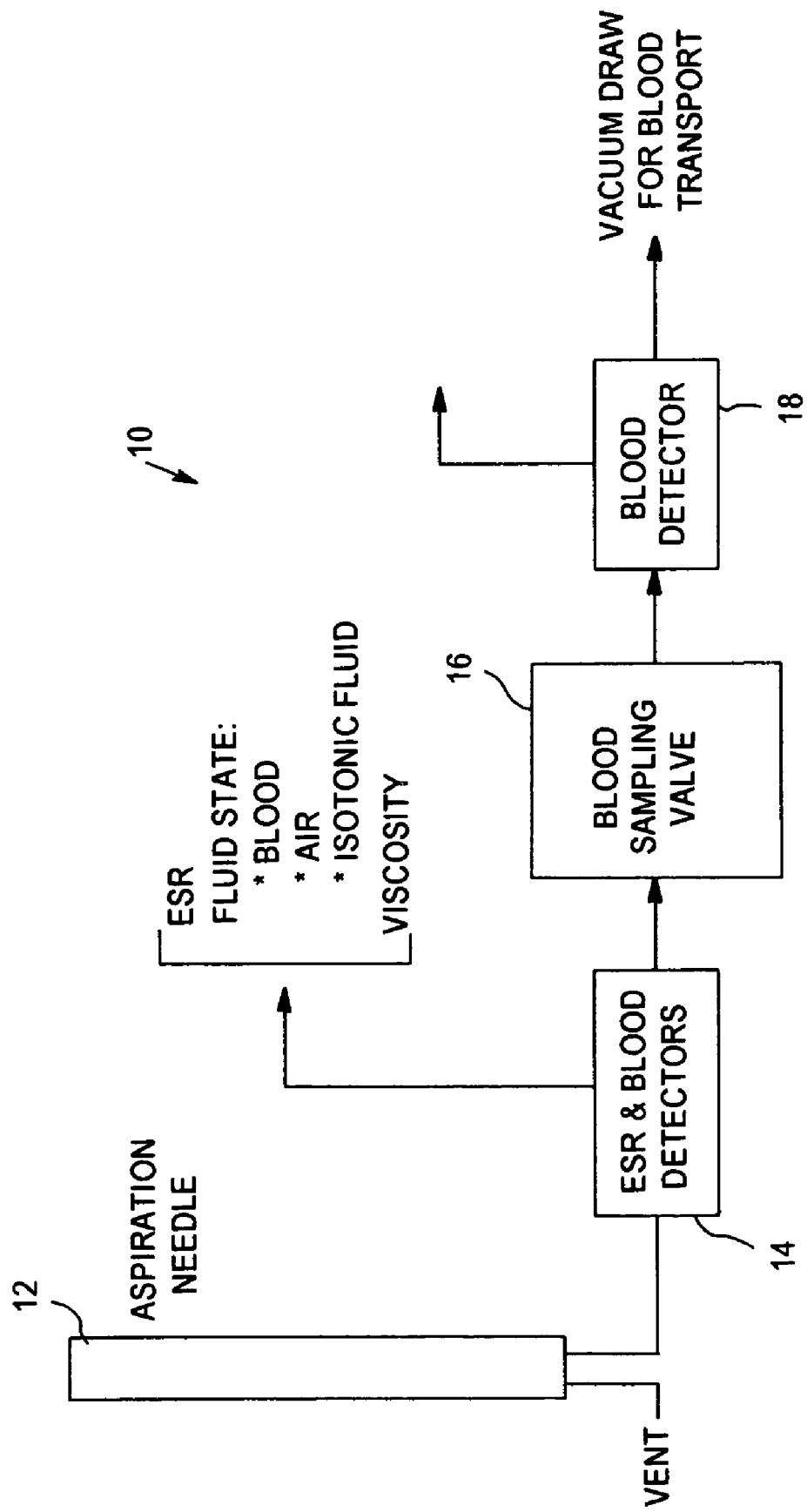
FIG. 1 is a schematic block diagram of a part of a so-called "non-suck-and-spit" type of hematology instrument according to the present invention.

The present invention relates to an apparatus and method for analyzing a blood sample in vitro. The apparatus can be configured, for instance, as a freestanding measurement device, or a sensor, detector, or device for use in a multi functional hematology instrument, or a sensor, detector or device for use in connection with an automated blood smear slide generator. The sensor, detector or device according to the present is utilized to analyze blood samples and is capable of determining one or more of the density/fluid-type of a fluid sample, the viscosity of a blood sample, and/or the erythrocyte sedimentation rate (ESR) and zeta sedimentation rate (ZSR) of a blood sample.

The present invention also relates to a multifunctional hematology instrument having one or more of the above referenced sensors, detectors or devices, and to an automated blood smear slide generator used in connection with one or more of the above referenced sensors, detectors or devices. In addition, the present invention relates to methods for determining the fluid-type of a fluid sample, the viscosity of a blood sample, and the erythrocyte sedimentation rate (ESR) and zeta sedimentation rate (ZSR) of a blood sample.

The above referenced sensors, detectors, devices, instruments and the like according to the present invention utilize a non-optic means for analyzing fluid contained in a capillary tube of the sensor, device, hematology instrument or the like. To this end, the device according to the present invention directs a waveform pulse at a known frequency transversely across the capillary tube and fluid sample and measures the flight of time of the pulse across the capillary tube and fluid sample and/or measures the Doppler shift of echo signals generated as a result of the pulse reflecting from particles, such as cells, within the sample. These measurements are utilized to determine various parameters of the fluid.

The waveform pulse can be, for instance, an ultrasonic pulse, a sound wave or acoustic pulse, or any other waveform that propagates at different rates depending upon the material through which the waveform travels. The waveform must also be one that enables Doppler shift measurements to be taken.

The transmission of sound through a medium occurs at different velocities depending upon the density of the material. The propagation velocity is proportional to the speed of sound in the fluid and the acoustic impedance of the fluid. Thus, since acoustic impedance varies with the product of the speed of sound and density, a signal proportional to density can be derived from observing the transit time of a sound through a medium. Thus, according to the present invention, a waveform pulse, such as an ultrasound pulse, is directed into a capillary tube of an instrument and the transit time, and in some cases the frequency shift, of the pulse, or the echo signal of the pulse, is received by one or more receivers and processed to determine one or more of the fluid-type within the tube, the viscosity of the blood sample within the tube, and/or the erythrocyte sedimentation rate (ESR) and zeta sedimentation rate (ZSR) of a blood sample within the tube.

U.S. Pat. No. 4,485,821 issued to Iinuma, U.S. Pat. No. 4,572,664 issued to Hanson and U.S. Pat. No. 5,409,010 issued to Beach et al. disclose examples of pulsed ultrasonic apparatus. The apparatus disclosed in the Iinuma and Beach patents relate to measuring blood flow in vivo of a patient. The disclosures of the Iinuma, Hanson, and Beach patents are herein expressly incorporated by reference.

Various embodiments, methods and concepts according to the present invention are each separately discussed below. These concepts include and relate to fluid type detection, viscosity determination, ESR and ZSR determination, and hematology instruments.

Fluid-Type Detection

Fluid-type detectors are commonly used in hematology instruments to determine whether air, isotonic fluid, or blood is present within a tube of the instrument at the detector location. There are two general forms of hematology instruments that differ in their method of sample aspiration and transport. These two general forms include a hematology instrument having an in-line vacuum draw with a sampling valve (see FIG. 1) and a so-called "suck-and-spit" type of hematology instrument (see FIG. 10).

An example of an in-line vacuum draw with sampling valve instrument is schematically illustrated in FIG. 1 in which a hematology instrument 10 has an aspiration needle, or syringe, 12 to draw a blood sample by vacuum from a closed vial (not shown). The sample is passed through a detector 14 to a blood-sampling valve 16, and then through a second detector 18 before being passed to other blood analysis sections (not shown) of the multifunctional hematology instrument 10. The detectors 14 and 18 are utilized to determine whether blood, isotonic fluid or air is in the line and to monitor the blood transport to ensure that a viable aspiration was achieved. In addition, the detectors 14 and 18 provide an indication when air is present in the sample column and when there is insufficient blood volume (ie., a partial aspiration condition).

Figure 10:
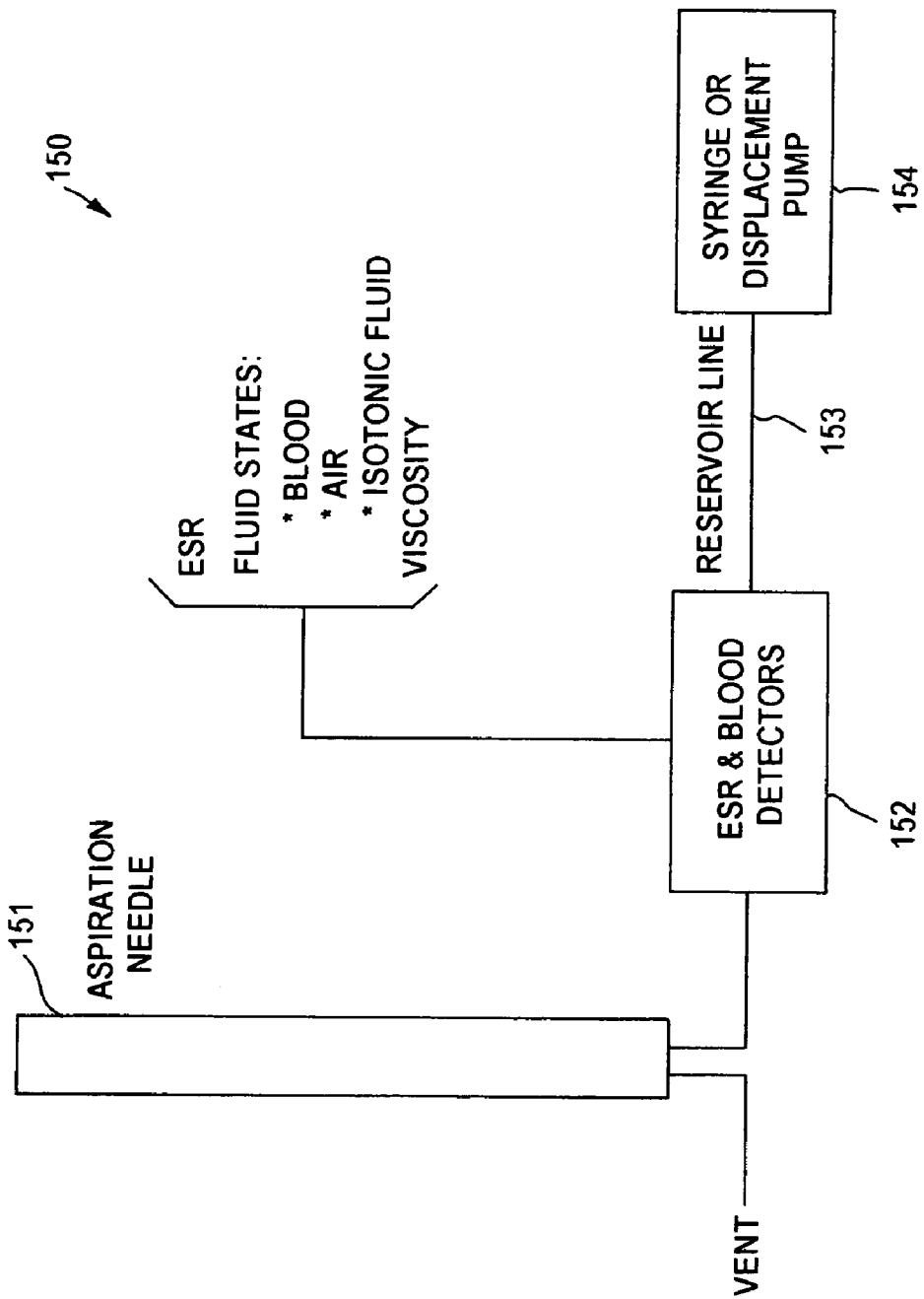
FIG. 10 is a schematic block diagram of a part of a so-called "suck-and-spit" type of hematology instrument according to the present invention.

An example of a suck-and-spit instrument is schematically illustrated in FIG. 10 in which a hematology instrument 150 has an aspiration needle, or syringe, 151 to draw a blood sample by a syringe, or displacement pump, 154 from a closed vial (not shown). The aspiration needle 151 is inserted into the closed vial from which the sample is drawn, and the sample is transported by action of the syringe, or displacement pump, 154 through a detector 152 and into a length of tubing, or reservoir line, 153. The draw is stopped after a desired volume of sample has been withdrawn from the closed vial. Thereafter, the aspiration needle 151 is withdrawn from the closed vial and moved to allow the sample, or a portion of the sample, to be dispensed into a receptacle, or receptacles. In addition, the direction of flow caused, for instance, by the displacement pump 154 can be reversed so that a desired volume of the sample can be dispensed to other blood analysis sections (not shown) of the multifunctional hematology instrument 150. The detector 152 is utilized to determine whether blood, isotonic fluid or air is in the line and to monitor the blood transport to ensure that a viable aspiration was achieved. In addition, the detector 152 provides an indication when air is present in the sample column and when there is insufficient blood volume (ie., a partial aspiration condition).

As previously discussed, optical density sensors are typically utilized in hematology instruments but have problems recognizing the difference between air and clear isotonic fluids and the conditions of air bubbles in the blood. In the first case, the optical difference between isotonic fluid and air is minimal, and in the second case, recognition of air bubbles contained within blood is problematic since blood is opaque. In addition, optical density sensors generally require an additional, separate glass tubing element at the optical measurement location that must connect and transition between plastic tubing extending from the aspiration needle and to downstream destinations of the sample. Thus, to overcome these and other problems, the detectors 14 and 18 according to the present invention utilize waveform pulses, such as ultrasound pulses, to determine the type of fluid in the tube as well as the leading and trailing edges of the blood sample and the presence or lack thereof of microbubbles.

Figure 2:
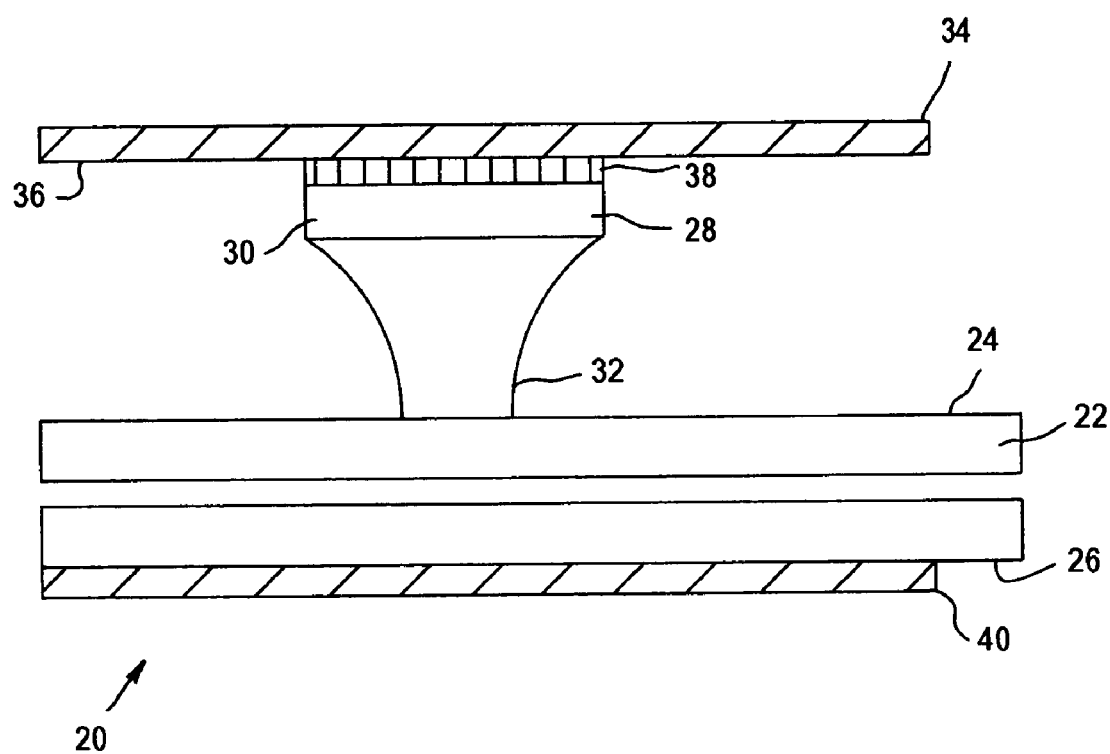
FIG. 2 is a view of a sensor assembly according to the present invention.

A fluid-type detector 20 according to the present invention is illustrated in FIG. 2. A sample tube 22 through which a sample is passed is illustrated in cross section and, as shown, has opposing proximal and distal walls, 24 and 26, respectively. For purposes of example only, the tube 22 can be made of polyurethane, have an inner diameter of between about 0.020–0.023 inch, and a wall thickness of about 0.030 inch. Of course, the detectors of the present invention can be utilized with smaller or larger tubes and with tubes made of different materials.

A sensor 28 is positioned adjacent a portion of the proximal wall 24 of the tube 22 to launch a pulsed signal, such as an ultrasonic chirp, transversely through the tube 22. The sensor 28 can be provided as a piezo crystal transducer 30 with a focusing cone 32 engaging the proximal wall 24 of the tube 22 to direct the piezo energy perpendicularly across a small section of the tube 22. In the illustrated embodiment, the sensor 28 is also utilized to receive a return echo signal of the pulse after the pulse makes a two-way pass through the tube 22 and sample fluid. Alternatively, a second sensor (not shown) can be located diametrically opposite sensor 28 relative to the tube 22 to receive the pulse after it makes a one-way pass through the tube 22 and fluid sample.

The sensor 28 and tube 22 are located within a housing 34. The housing 34 includes a mounting reference wall 36 on which the sensor 28 is mounted via a damping pad 38. The illustrated housing 34 also includes a rear wall 40 that engages the distal wall 26 of the tube 22 and that causes the launched pulse to be reflected back to sensor 28. The housing 34 is preferably made of a high-density material, such as steel, to prevent external signals from reaching the sensor 28 and to ensure a high reflection of the launch signal off the rear wall 40. The damping pad 38 is utilized to absorb signals projected therein so that no reflection occurs off the mounting reference wall 36. Thus, the damping pad 38 should have a medium density and be lossy to the launch signal frequency. All coupled energy should be dissipated as heat. The damping pad 38, for instance, can be a gasket-type material containing a high concentration of nickel-coated carbon particles within a silicon rubber carrier. The metal-coated particles within the silicon carrier additionally provide an electrically conductive path, allowing connection with the piezo sensor.

The piezo crystal transducer 30 grows dimensionally with the application of an electrical potential, and optimally, the growth is in the thickness of the crystal. Since a piezo crystal grows to either side thereof, the sensor 28 should be mounted to force the growth to occur to one side. The size of the crystal of the transducer 30 should be selected so that the crystal is self resonant with the launch frequency to ensure the piezo crystal operates with maximum coupling between mechanical motion and electrical interface. A coupling gel (not shown), such as silicon grease, should be utilized between the tube 22 and focusing cone 32, which acts as a matching medium between the crystal and the tube 22. The density of the tube 22 and focusing cone 32 should be similar to achieve maximum sensitivity of the sensor. For example, the focusing cone 32 can be magnesium or a magnesium alloy that has a density similar to the density of the tubing. (See Table 1, below).

The transit, or flight, time of the waveform pulse, such as an ultrasound pulse or chirp, launched from the sensor 28 into the tube 22 and reflected back to the sensor 28 from the distal wall 26 of the tube 22, or the rear wall 40 of the housing 34, depends on the densities of the mediums through which it travels. For example, Table 1 provides the density (ie. specific gravity) of selected materials.

TABLE 1

| Material | Density (grams/cm$^3$) |
|---|---|
| Steel | 7.7 |
| Magnesium | 1.76 |
| Fresh Water (type 1 distilled) | 1.000 |
| Salt water (sea at zero alt.) | 1.03 |
| Polyurethane | 1.12 |
| Air (32° C., 1 atm) | 0.001294 |

Blood has a density similar to salt water, and the densities of blood, isotonic fluids (ie. salt water), and polyurethane tubing are all substantially the same. For an ultrasound pulse to change its flight time through a sample medium, a substantial change in density of the medium is required. Thus, when the density of the fluid sample and tubing 22 are close in value, the boundary, or transition, between the fluid sample and tubing 22 is not observable (ie. no significant reflection of the pulse at the transition). As stated previously, the typical fluid sequence through the tubing 22 is air, isotonic fluid, blood, isotonic fluid, and then air. When air is present in the tube 22 at the fluid-type detector 20 location, the fluid-type detector 20 can readily determine and self calibrate for the inner and outer diameter dimensions of the tubing 22 since the density change at the air-to-tube transitions are significant and provide readily recognizable echo signals. Thus, the fluid-type detector 20 functions as a tubing diameter detector when air is present in the tube, and thereafter, the isotonic fluids and blood are processed without the need to observe the boundary conditions of the tubing 22 and fluid sample.

The propagation velocity of sound through various materials is summarized below in Table 2.

TABLE 2

| Medium | Propagation velocity in the Medium |
|---|---|
| Air (dry) | 331.45 m/s |
| Salt Water (36 ppt salinity) | 1505 m/s |
| Blood | 1500–1650 m/s |
| Coupling Gel | 1540 m/s |

The propagation velocity of sound through blood ranges from 1500–1650 m/s depending upon the density of the blood and is substantially the same as the propagation velocity of sound through isotonic fluids (ie. salt water). The propagation velocity of sound through air is much less than that of blood and isotonic fluids, and thus, the presence of air within the tube 22 can readily be determined from the flight time measurement of the pulse. Although blood and isotonic fluids have similar density and propagation velocity values, the reflections, also referred to as noise, from the two fluids are considerably different and readily observable.

Isotonic fluid is homogeneous and does not reflect any of the launched pulse except possibly at transition boundaries with the tubing 22. Of course, this is only true if the isotonic fluid does not contain microbubbles. For instance, if the isotonic fluid is heated or has been shaken in its container shortly before its use, microbubbles may be present in the isotonic fluid. The presence of microbubbles in the isotonic fluid is undesired since the microbubbles will distort the efficacy of the red and white cell counts due to the bubbles appearing as cells. Thus, for successful operation of the instrument, care should be taken to ensure that the isotonic fluid is free of microbubbles.

In contrast, blood carries a slurry of high-density bodies including cells, lipids and other constituents along with serum, and blood generates numerous reflections from all of the slurry objects. Thus, since the distance from the transducer 30 to the distal wall 26 of the tube 22 is constant and can be determined when air is present within the tube 22, the identification between blood and isotonic fluids in the tubing 22 can readily be determined by observing the presence or lack thereof of noise reflections of the launched pulse from particles within the fluid.

Figure 3:
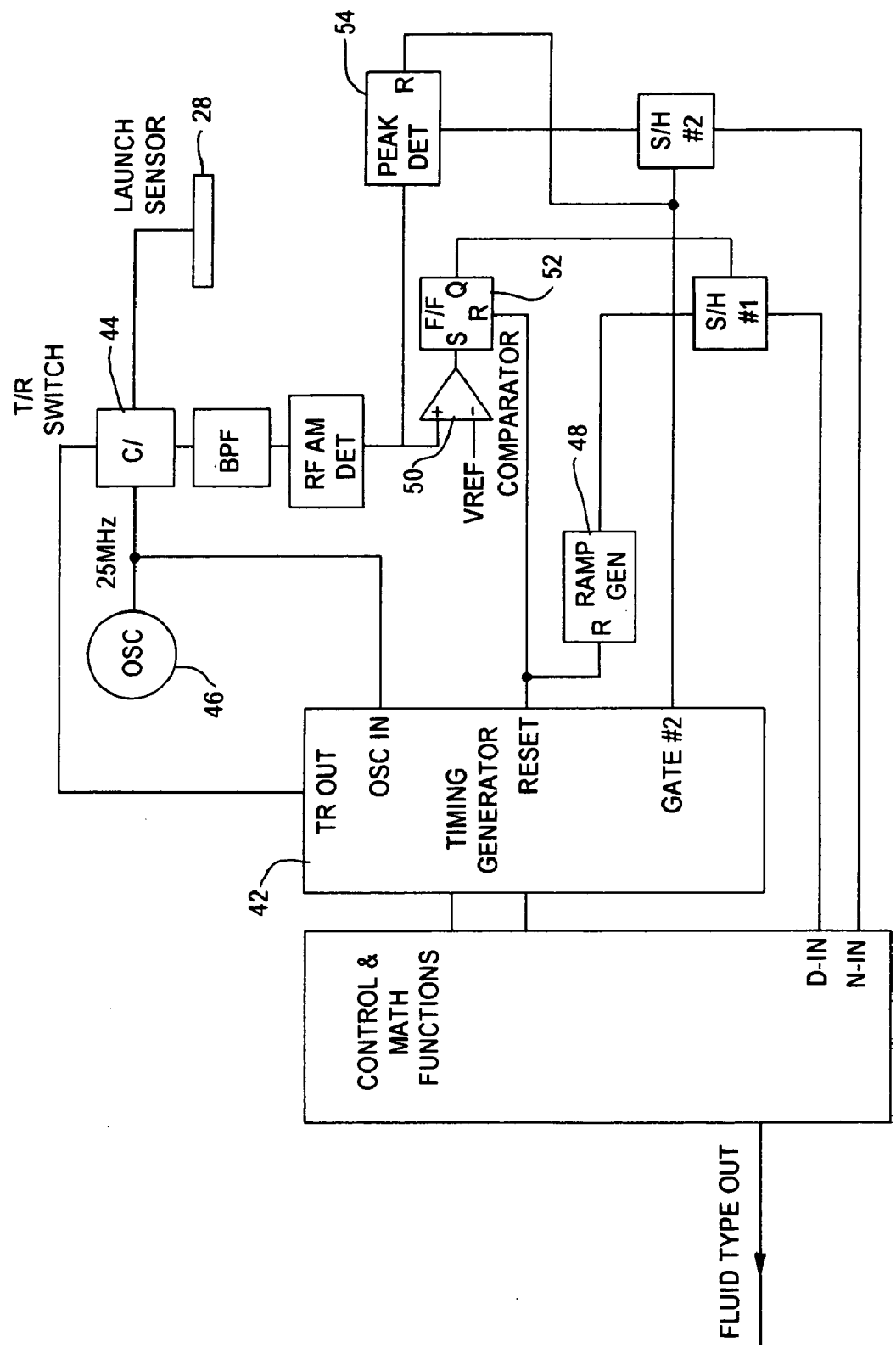
FIG. 3 is a circuit block diagram of the operation and controls of the sensor illustrated in FIG. 2.

The operation and control of the fluid-type detector 20 is best illustrated in FIG. 3. A timing generator 42 opens a transmit/receive switch 44 for a single complete cycle of a 25 MHz oscillator 46 and enables the sensor 28 to launch a pulse toward the tube 22 through the focusing cone 32 (see FIG. 2). A minor reflection is generated at the transition between the focusing cone 32 and the tubing 22 due to the difference in density of the tubing 22 and focusing cone 32. However, most of the launch pulse signal will continue to propagate through the tubing 22 and into the fluid sample contained therein. The launch pulse signal will propagate through the fluid sample until it hits the distal wall 26 of the tube 22. If the sample fluid is air, a large reflection is generated at the distal wall 26 because of the transition from air to the solid distal wall 26 of the tube 22. If the sample is an isotonic fluid or blood, the majority of the launch pulse signal will continue to propagate into the distal wall 26 of the tube 22 because of the similar densities of the tube 22 and fluid samples. This pulse will reach the rear wall 40 of the housing 34 and be reflected therefrom due to the large change in density between the transition of the polyurethane tube 22 and steel rear wall 40. All of the above referenced reflections are received by the sensor 28.

The fluid-type detector 20 self calibrates when air is present within the tube 22. When this happens, the flight time of the echo from the distal wall 26 of the tube 22 is significantly longer than that compared to when isotonic fluid or blood is located within the tube 22 due to the slower propagation velocity of the signal in air. In addition, two large echos are received, one from the distal wall 26 of the tube 22 and the other from the rear wall 40 of the housing 34. The tubing wall thickness is readily determined from the above referenced echo signals and the known overall geometry of the components in the signal path. The tubing inner diameter is readily determined (even if the tubing is slightly compressed) since the mechanical assembly has fixed geometries and since the tubing inner diameter is the only variable remaining to be calculated.

An early arrival of the echo signal from the rear wall 40 of the housing 34 indicates that isotonic fluids or blood has replaced air in the tubing 22 at the location of the detector 20. The different density and propagation values of air and isotonic fluids, or blood, cause a significant change in the reflections received by the sensor 28 and permit the sensor 28 to readily identify the transition from air to isotonic fluid, or blood. To this end, when the pulse is initially launched, the timing generator 42 resets a ramp generator 48. See FIG. 3. When the echo signal from the rear wall 40 of the housing 34 is received by the sensor 28, it cause a sample/hold #1 to freeze the value of the ramp signal. The captured value of the ramp signal is a function of the flight time of the echo signal (times two due to the two-way pass) passing completely through the tube 22 and fluid sample and is utilized to determine the density of the fluid. Receipt of the relatively large echo from the rear wall causes a comparator 50 to toggle an RS flip-flop 52.

A significant amount of small echo signal noise is received by the sensor 28 when blood is present within the tubing 22, while air and isotonic fluids do not generate such noise. The presence of such noise is determined with a peak detector 54 that is gated during a time period when noise echo signals generated from within the tube 22 are expected to be received by the sensor 28. When the noise echo signals from within the tube 22 are expected to cease and the launch signal has reached the distal wall 26 of the tube 22, the peak detector 54 is reset and a sample/hold #2 freezes the noise value. Thereafter, the outputs of the sample/holds #1 and #2 are digitized, and the data processed to determine and report the contents of the sample tube as air, blood, or isotonic fluid.

The presence of microbubbles is a condition that must be capable of being recognized and reported by the fluid-type detector 20. Microbubbles cause considerable problems in blood analyzing instruments since the bubbles are often the same size as cells and can lead to errors, for instance, in the size counting of cells. The presence of microbubbles in isotonic fluid can occur due to rough handling of reservoir containers that are being exchanged at the hematology instrument. Microbubbles can also be generated within isotonic fluid when reservoir containers are exposed to significant increases in heat as might occur when moved from cold storage to a heated laboratory. The presence of microbubbles in blood samples is a common problem and is typically caused by excessive agitation of the blood sample before aspiration, such as by over shaking the sample tube.

The detector 20 according to the present invention detects the presence of microbubbles in a blood sample and/or isotonic fluid by observing that the flight time of the launch pulse is longer than expected and that the density of the fluid sample is less than expected. Also, considerable variation between successive measurements will be observed since the bubbles will not be evenly distributed in the fluid column and since reflections will be generated from the air bubbles themselves due to the step change in density seen by the ultrasonic pulse. Thus, the measured time of flight and/or density values are compared to acceptable values stored in memory, and successively obtained time of flight and/or density value measurements are compared to determine if a variation therebetween is within an acceptable range. Thereafter, the fluid-type detector 20 reports the fluid-type and, in addition, reports whether or not microbubbles are present within the blood sample and/or isotonic fluid.

Therefore, the fluid-type detector and corresponding method of detecting fluid-type as described above can be utilized to measure the density and recognize the contents of a fluid within a tube of an instrument. The detector and method can also recognize the presence of microbubbles in a blood sample and isotonic fluid and can detect the leading and trailing edges of the blood aspiration. The detector is self-calibrating and self-correcting for changes in tube dimensional variations. In addition, the detector can launch a signal into the same tubing, for instance, plastic tubing, that typically leads from the aspiration needle to a destination downstream of the detector, as illustrated in FIG. 1.

Viscosity Determination

A measurement of the viscosity of a blood sample is required in various blood processing procedures. For instance, a viscosity measurement can be utilized to determine the proper hold time, smear velocity and acceleration of a wedge of a slide-making instrument to produce a desired smear of a monolayer of cells on a slide. In addition, a viscosity measurement can be utilized in a multifunctional hematology instrument to determine the optimal dilution of a blood sample, for instance, to optimize sample processing time for cell counting and white and red cell separation procedures.

The viscosity of blood in a tube can be determined from the density of the blood and the velocity of the blood flowing within the tube. Viscous flow is described as each particle moves in a direction parallel to the boundary of the enclosing channel, or tube. The force that opposes viscous flow of a liquid is known as the resistance to distortion. In the case of a viscous flow through a tube, it is assumed that there is no molecular slippage of the liquid at the tube surface. The laws of viscous flow may be applied to determine the velocity and flow in tubes. The viscosity, Poise, is defined in units of $dyne*sec/cm^2 = gram*sec/981\ cm^2$. The relationship within a tube is:

$$Poise = \pi(\text{delta pressure in tube})h^4/(125568(\text{length of tube})(\text{flow in tube}))$$

where h=diameter of tube.

The above referenced variables can be determined as follows according to the present invention. As best illustrated in FIG. 1, one side of tubing adjacent the aspiration needle 12 is at atmospheric pressure. In practice, the vent side of the aspiration needle will impose a restriction to the ambient air. The restriction will introduce a consistent drop, so that the air pressure within the sample tube will be offset from ambient atmospheric pressure by a predicable value based upon the vent tube aperture and length. Thus, the delta pressure is equal to either the sucking vacuum or vent tube pressure source and can be readily determined. A detector 14 for measuring viscosity is located about the tubing a fixed distance from the aspiration needle 12. The fixed distance is readily determined. The detector 14 measures the diameter of the tube when air is present in the tube as discussed with respect to the fluid-type detector 20 of the present invention.

Flow in the tube is determined by measuring the density of the blood and the velocity of the blood by the detector 14. The detector 14 measures the density of the blood as discussed with respect to the fluid-type detector 20 of the present invention and determines from the density measurements the timing needed to capture the desired flow velocity measurements. The detector 14 measures the velocity of the blood sample by measuring the Doppler shifts of echo signals of a waveform pulse, such as an ultrasound pulse, launched into the sample flow and reflected from cells located at least two different points within the cross-section of the fluid sample to enable a cross section flow velocity profile to be approximated. This is discussed in greater detail below. From these measurements, the flow volume, and ultimately the viscosity, are determined.

It is necessary to determine the flow rate of the fluid through the tube by at least a two-point velocity measurement since fluids transported through a tube do not undergo a constant velocity at any point within the cross section of the inner diameter of the tube, for instance, the velocity at the tube wall is always zero. The flow velocity takes a cross sectional shape similar to that of a Gaussian curve and can be determined, for instance, from a two-point measurement. Flow rate of the sample fluid is then developed from the shape of the obtained curve. The two points of interest are the center of the tube inner diameter and a second location between the center and the inner diameter wall of the tube. The velocity of the fluid at any point across the cross section can be determined from the Doppler shift that results from the collision between a launch pulse of a known frequency and the velocity of the fluid at that point in the cross section. The highest frequency measured will be that of the flow closest to the center of the flow.

Figure 4:
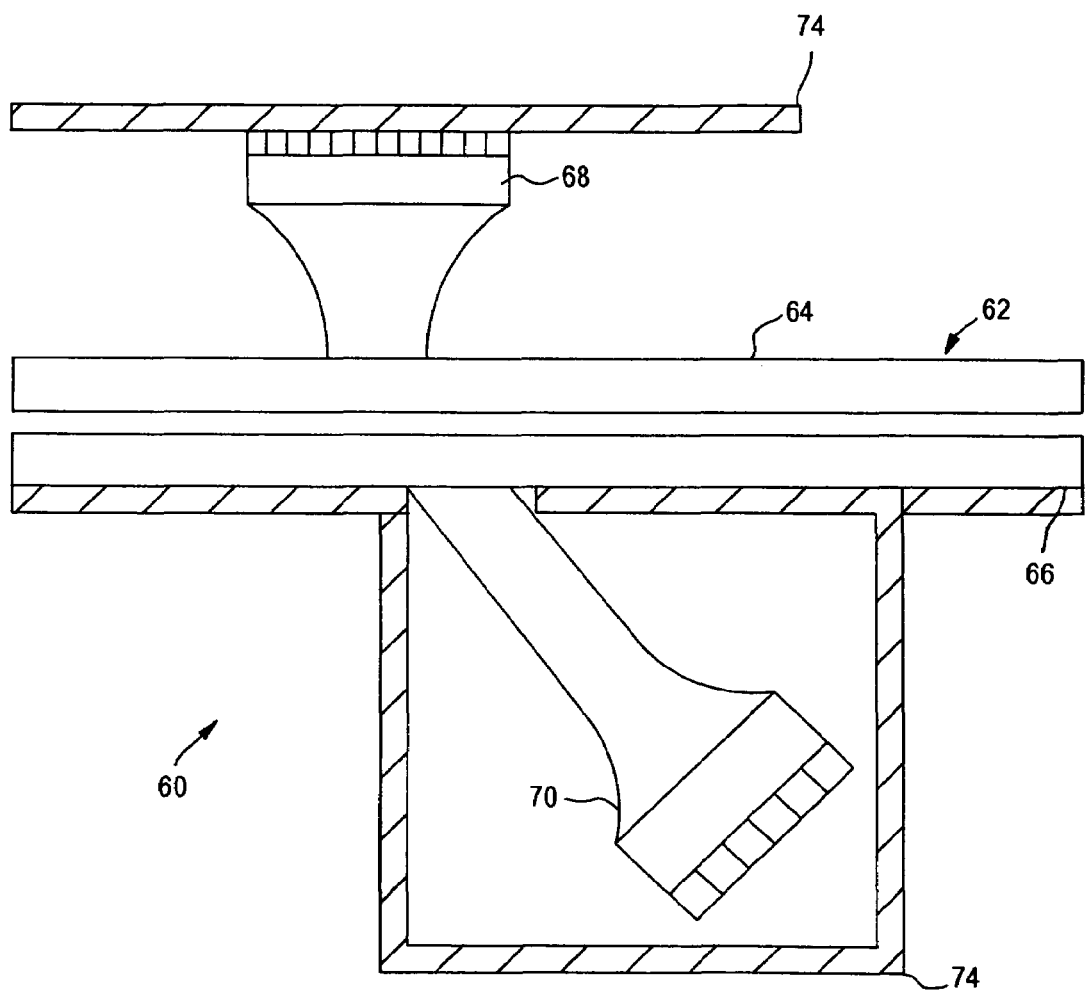
FIG. 4 is a view of a second embodiment of a sensor assembly according to the present.

A viscosity detector 60 according to the present invention is best illustrated in FIG. 4. A sample tube 62 through which a sample is passed is illustrated in cross-section and, as shown, has opposing proximal and distal walls, 64 and 66, respectively. The viscosity detector 60 includes a pair of sensors, 68 and 70. The density/launch sensor 68 is substantially identical to the fluid-type detector 20 discussed in detail with respect to FIG. 2. The density/launch sensor 68 is positioned adjacent a portion of the proximal wall 64 of the tube 62 to launch a pulsed signal, such as an ultrasonic chirp, through the tube 62 and to receive the echo thereof. The sensor 68 can be provided as a piezo crystal transducer that engages the proximal wall 64 of the tube 62 to direct the piezo energy perpendicularly across a small section of the tube 62. The sensor 68 is utilized to measure the fluid-type/density of the fluid within the tube 62 and the diameter of the tube 62 when air is present within the tube 62 as previously discussed.

The second sensor 70 is a Doppler sensor and provides a function of receiving a Doppler shifted signal which results from the collision of the signal launched from sensor 68 with the forward moving particles in the blood sample within the tube 62. In FIG. 4, forward movement is defined as a movement from left to right on the drawing. As shown in the drawing, the Doppler sensor 70 engages the distal wall 66 of the tube 62 and is positioned at an angle relative to the longitudinal axis of tube 62 and relative to the direction of the pulse launched into tube 62. The Doppler sensor 70 can be positioned on the same, or opposite, side of tube 62 relative to the density sensor 68. A high density housing 74, such as a steel housing, encloses the sensors 68 and 70 and a portion of tube 62. Damping pads are utilized on sensors, 68 and 70, for reasons previously discussed. A coupling gel (not shown), such as silicon grease, can be utilized where the tube 62 engages the sensors 68 and 70.

Figure 5:
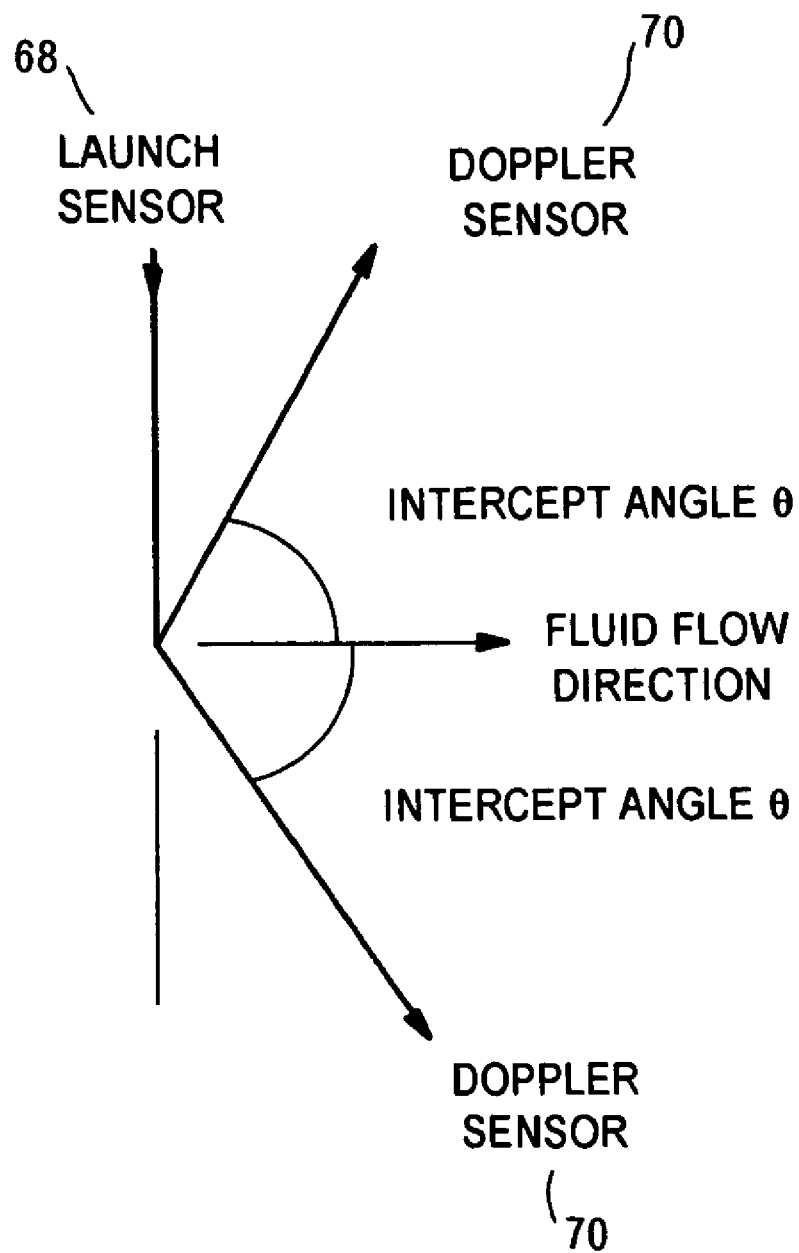
FIG. 5 is a diagram schematically illustrating the operation of the sensor assembly illustrated in FIG. 4.

Doppler sensor 70 must be positioned at an angle θ relative to the central longitudinal axis of the tube 62 so that it is capable of observing the Doppler shift. The angle cannot be zero. FIG. 5 illustrates the relationship between the launch signal and two possible Doppler sensor positions. At any intercept angle θ, the amount of Doppler frequency shift is:

$$\Delta f = 2VF_o \cos \theta / C$$

where: V=velocity of the colloidal particles in the fluid,
$F_o$=transmitted carrier frequency,
θ=intercept angle, and
C=velocity of sound in the fluid column.

There is a constraint on how large the intercept angle can be as it approaches a right angle. This is dictated by the requirements of non-disturbance of the fluid flow and the amount of tubing wall distance the Doppler signal must pass. Since the tubing walls are not a hard material, it will present transmission loss to the signal. Therefore, a nominally optimum intercept angle is one that balances the delta frequency change and the signal amplitude. In addition, a minor correction to the signal received by sensor 70 must be made to account for the path shift of the signal in the tubing wall due to the difference in material density. This correction is described by Snell's Law, which accounts for the change in vector path that occurs when there is a change in density between two or more mediums.

The launch pulse utilized to measure the density is different than the launch pulse utilized to measure the Doppler shift. In the density measurement, it is only necessary to determine the flight time of the return echo, and a single cycle of the launch carrier frequency is preferred because it prevents echo interference. For the Doppler shift measurement, a four-cycle burst of the carrier signal can be utilized to allow the delta frequency measurement to stabilize. Since all the dimensions at the viscosity detector 60 are substantially constant, the pulse rate frequency, PRF, can be preset for best performance and post signal processing can be blanked at all times other than during measurement window time. This eliminates the potential of receiving false echos.

It is desirable to set the carrier frequency as high as possible to gain insight from the motion of cells within the blood sample. An example of an operation frequency useful with the present invention is 25 MHz. At this operation frequency, the observable feature size capability of the Doppler sensor is approximately 40 nsec, which translates to object sizes of approximately 0.00235 inch. It is also desirable that the self-resonance of the sensors 68 and 70 match that of the master oscillator. An example of a piezo material for use in making the Doppler sensor 70 is a PZT (Lead Zirconate Titanate) material that can operate with a single high Q self resonance point within the frequency range of interest and be made in a desired relatively small size. The pulse rate frequency, PRF, can be set, for example, in a range of 2 to 100 usec.

Figure 6:
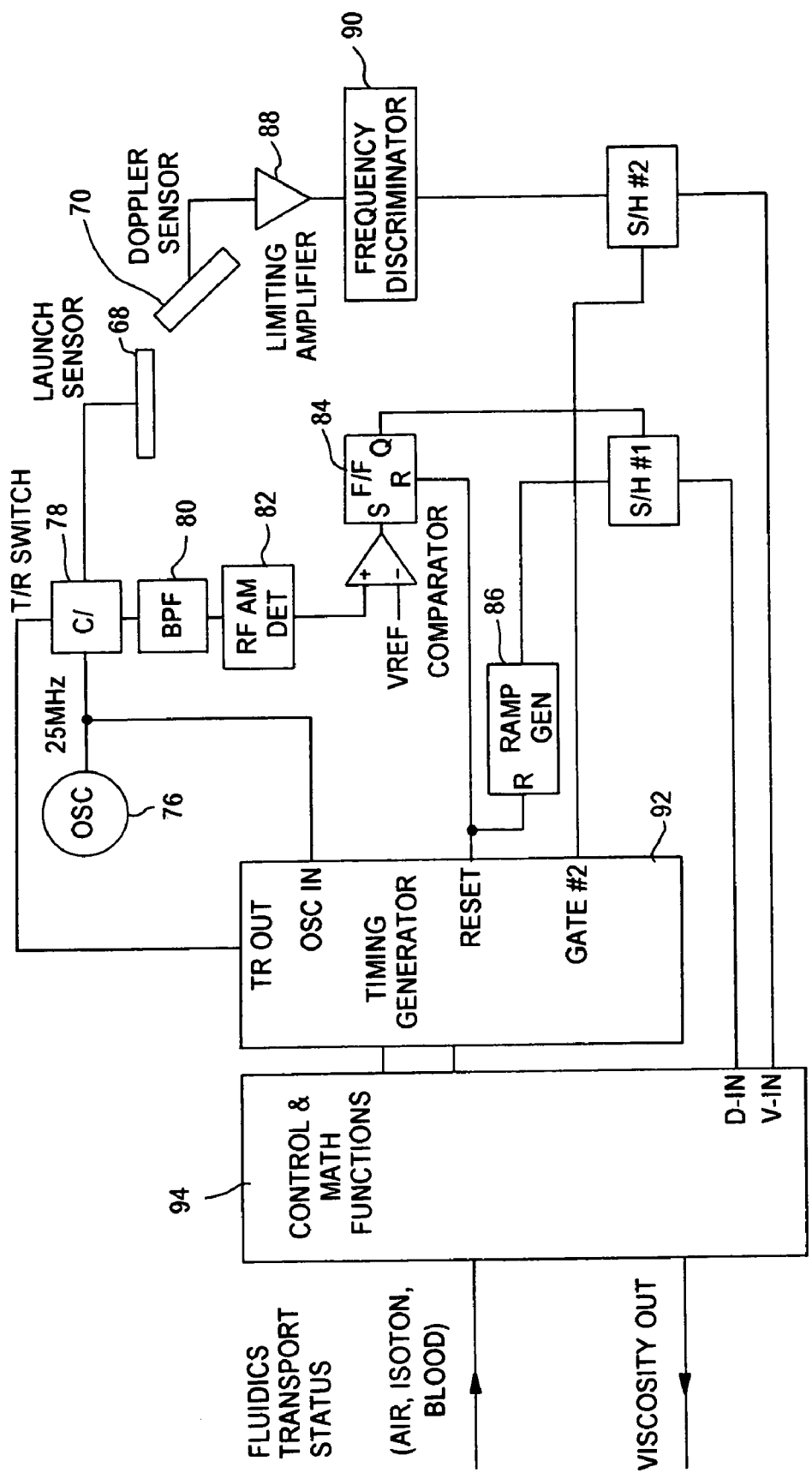
FIG. 6 is a circuit block diagram of the operation and controls of the sensor illustrated in FIG. 4.

The control of the viscosity detector 60 is best illustrated by the circuitry block diagram of FIG. 6. The master oscillator 76 is a 25 MHz sine-wave source. A transmit/receive switch 78 determines whether or not a single or four-cycle burst signal is supplied to and launched by sensor 68 through tube 62. In a receive mode, the echo received by sensor 68 is processed through a bandpass filter 80 and an AM detector 82 such that the voltage output of the AM detector 82 is a function of the echo amplitude. The echo received by sensor 68 from the steel housing 74 is relatively large, and when received, causes an RS flipflop 84 to close the sample/hold #1 to record the amplitude from a ramp generator 86. After a pulse is launched, the RS flipflop 84 and ramp generator 86 are reset after a time delay. The delay is to ensure that any echo from the transition between the sensor 68 and tubing 62 is ignored. The voltage latched by sample/hold #1 is the propagation time of the pulse times two. This is utilized to determine the density of the fluid and the timing for sample/hold #2.

Following the determination of the sample density, a four-cycle burst is caused to be launched by sensor 68 into the tube 62. The Doppler sensor 70 recovers the product of the launched carrier frequency and the velocity of the blood cells. This is processed through a limiting amplifier 88 that delivers a constant amplitude signal to a frequency discriminator 90 to develop a voltage that is proportional to the frequency shift caused by the Doppler effect. Sample/hold #2 is gated to capture the Doppler signal at predetermined times within a narrow window of time. The predetermined times correspond to a signal from the center of the tube 62 and a signal about 25% or 75% into the tube 62. This may be accomplished in a single chirp event, or two sequential operations. The master oscillator 76 is used to sequence the operations of the timing generator 92 and the control and math functions block 94. Preferably, the frequency discriminator 90 operates in an open loop mode, and the sample/hold #2 is capable of latching the output of the frequency discriminator 90 in an 80 nsec period to provide desired spatial accuracy for the velocity determinations.

By way of example, a nominal aspiration flow velocity is expected to be approximately 100 uL/sec, and for a 0.023 inch inner diameter tube, the average flow velocity will be about 0.373 mm/sec. If the incident angle is 30° and the velocity of sound through the blood is 1600 m/sec, the Doppler delta frequency is about 10 Hz. The peak velocity is likely to cause a Doppler shift as high as 50 Hz. The use of a direct frequency discriminator 90 is utilized to process this frequency shift in a quick manner. U.S. Pat. No. 3,292,093, for instance, discloses a suitable example of a frequency discriminator.

The viscosity measurements can be taken continuously so that the viscosity detector 60 can recognize the leading the trailing edges of the blood sample aspiration. A position within the blood sample aspiration that is homogenous can also be identified. Thus, the viscosity measurements can also recognize partial aspiration conditions since bubbles will be detected in such an aspiration.

Therefore, the above referenced viscosity detector and method of detecting viscosity can be utilized to measure the density, velocity, and viscosity of a fluid within a tube of an instrument. Such measurements are required, for instance, in blood smear slide making apparatus and in multifunctional hematology instruments. The detector and method can also recognize the presence of bubbles in a blood sample aspiration, detect the leading and trailing edges of the blood aspiration, and determine where the sample is homogenous. The detector is self-calibrating and self-correcting for changes in tube dimensional variations and can be utilized in connection with the same tubing that leads uninterrupted from an aspiration needle to a destination downstream of the detector.

ESR and ZSR Measurements

Figure 7:
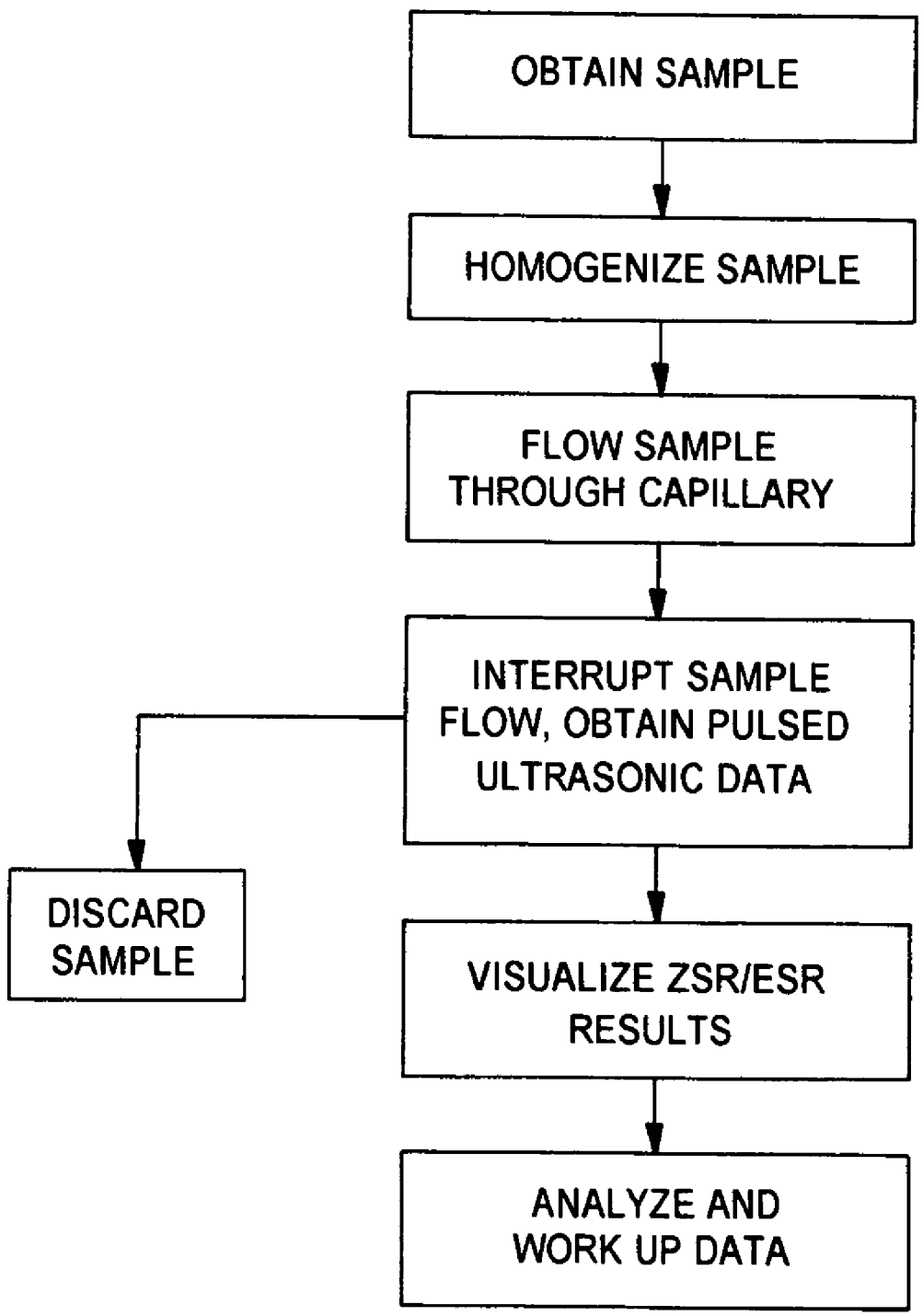
FIG. 7 is a flow diagram of a method of measuring the sedimentation rates of a blood sample according to the present invention.

The ESR is a measure of the degree of settling of erythrocytes in plasma within an anticoagulated whole blood specimen during a period of time, and the ZSR is a measure of the packing of erythrocytes under a standardized stress. According to the present invention, both can be simultaneously measured utilizing an assembly, for instance, as illustrated in FIG. 4 and a method, for instance, as illustrated in FIG. 7. To this end, a column of blood flowing within a tube is suddenly stopped and the deceleration of the cells within the plasma is monitored by launching a waveform pulse having a known frequency, such as an ultrasound pulse, into the tube and by receiving and processing the return echo signals.

During a steady state transport mode of the blood sample, cells will be concentrated within the center of the tube while plasma will be dominate at the walls of the tube. When the blood sample column is suddenly stopped, the cells will continue to move forward until frictional losses in the plasma absorb the kinetic energy of the cells. Ultimately, the cells will dissipate into a homogenous distribution of cells and plasma until gravity causes the cells to settle out of suspension. The cells carry an electrostatic charge, the zeta potential, which is a function of the protein composition of the plasma. The zeta potential will cause the cells to spread apart, and therefore, cell deceleration will occur simultaneously in both forward and transverse directions within the tube. When the column is initially stopped, the transverse velocity of the cells will peak and then decay as the cells come to an equilibrium distribution state. The peak transverse velocity will occur before the forward motion of the cells ceases.

The rate of erythrocyte settling is dependent upon the protein composition of the plasma, the size and shape of the erythrocytes, the concentration of erythrocytes, and the temperature of the blood sample. For example, higher amounts of proteins present in the plasma and higher erythrocyte concentration will reduce ESR. Macrocytes will settle at a faster than normal rate, and microcytes and irregularly shaped poiliocytes will settle at a slower than normal rate. The temperature of the blood sample will affect the viscosity of the plasma, which in turn will affect the ESR. In addition, an anemic individual (low blood cell count) will appear to have an increased ESR. The ESR and ZSR detector according to the present invention is capable of properly accounting for all of the above conditions.

The ESR and ZSR detector according to the present invention can be assembled identical to that illustrated in FIG. 4 relative to the viscosity detector 60. To this end, the ESR and ZSR detector has a launch sensor directed perpendicularly at a tube and a Doppler sensor canted at an angle θ relative to the tube. These sensors can be a single multiplexed sensor or a pair of separate sensors. During the time the blood sample is in steady state transit and is flowing in the tube past the ESR and ZSR detector, the density and viscosity of the blood sample is determined. See the discussion of the fluid-type detector 20 and the viscosity detector 60 for a description of how these determinations are made. Inconsistencies of the aspiration sample, the presence of microbubbles, and incomplete aspiration conditions can also be detected at this time as previously discussed.

An aspiration draw of a blood sample is taken form a storage vial, or the like. Preferably, the sample is a mixture of whole blood and $K_3ADTA$ drawn atraumatically within no more that 30 seconds and is the same as that typically utilized in most automated blood analysis instruments. A syringe or positive displacement pump can be utilized for drawing the sample, or the aspiration can be drawn by vacuum or by pressurization of the vial. During this steady state flow condition in which the blood sample flows at a substantially constant velocity, the cells become bunched in the center of the fluid column within the capillary tube. The steady state rate of flow of the blood is not critical since the ESR and ZSR measurements are relative measurements. After the aspiration draw has withdrawn a sufficient amount of blood sample, the blood column within the tube is abruptly stopped. At this time, the ESR and ZSR detector monitors the deceleration, or rate of decay, of the forward and transverse motion of the cells within the plasma. The forward Doppler sensor monitors the forward motion of the cells and the launch sensor monitors the transverse motion of the cells. These monitoring functions are accomplished by measuring the Doppler shift (ie., change in frequency) of the echo signals reflecting off moving cells. The necessary measurements to determine ESR and ZSR values of the blood sample are completed before the velocity of the blood cells reaches zero, and preferably within 30 seconds.

Data collected during the viscosity measurement provides the timing for the Doppler shift measurements and permits the temperature dependence of cell deceleration to be compensated for within the ambient temperature range of 60–90° F. in which most hematology instruments are operational. During both the viscosity measurements and Doppler shift measurements of the ESR and ZSR detector, cell velocity data is measured at fixed spatial positions within the capillary tube. For example, forward cell motion is monitored at the center of the tube and transverse cell motion is monitored at a point about 25% from the inner diameter of the tube. The density measurement provides information to the detector concerning the location of the near and far inside edges of the tube relative to the flight time of the launched pulse. Thus, knowledge of the density of the blood sample and the relationship of the angle between the launching sensor and the forward Doppler sensor permits the center of the tube, as observed by the forward Doppler sensor in time, to be calculated.

Figure 8:
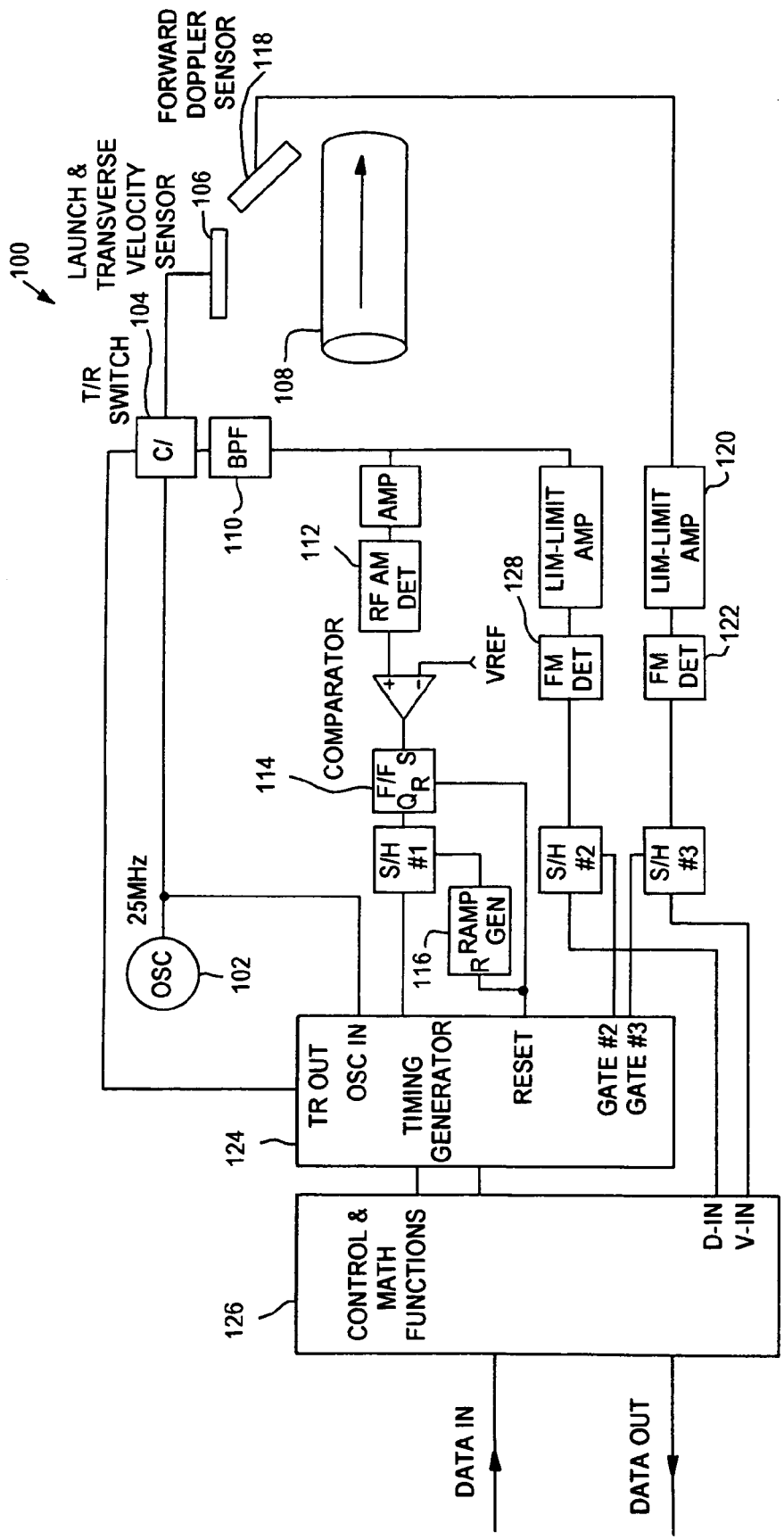
FIG. 8 is a circuit block diagram of the operations and control of a dual sensor ESR/ZSR detector according to the present invention.

The circuit block diagram of FIG. 8 best illustrates the operation and control of an ESR and ZSR detector 100. The master oscillator 102 is a 25 MHz sine-wave source. A transmit/receive switch 104 determines whether or not a single or four-cycle burst signal is supplied to and launched by sensor 106 through tube 108. In a receive mode for a single signal launched into a fluid flowing at a constant velocity within the tube 108, the sensor 106 is utilized to receive the echo of the signal, and the received echo is processed through a bandpass filter 110 and through an AM detector 112 such that the voltage output of the AM detector 112 is a function of the echo amplitude. The echo of interest is that received from the far steel wall of the housing of the detector 100. This echo can readily be recognized because it has a relatively large amplitude due to the relatively high density of the steel housing in comparison with the relatively low density of the wall of the tubing 108. Receipt of this echo causes an RS flipflop 114 to close a sample/hold #1 (S/H #1) to record the amplitude of a ramp generator 116. After a pulse is launched, the RS flipflop 114 and ramp generator 116 are reset after a time delay to ensure that any echo from the transition between the sensor 106 and tubing 108 is ignored. The voltage latched by sample/hold #1 provides information of the propagation time of the pulse times two. This is used to determine the density of the fluid in the tube and the timing for sample/holds #2 and #3 (S/H #2 and S/H #3). It is also utilized to measure the dimensions of the tube 108 when air is present in the tube.

Following the determination of the sample density and while fluid is flowed at a substantially constant velocity within the tube 108, a four-cycle burst is caused to be launched by sensor 106 into the tube 108. The forward Doppler sensor 118 recovers the product of the launched carrier frequency and the forward velocity of the blood cells. This is processed through a limiting amplifier 120 that delivers a constant amplitude signal to a frequency modulation, FM, detector 122 (ie., frequency discriminator) to develop a voltage that is proportional to the frequency shift caused by the Doppler effect. Sample/hold #3 is gated to capture the Doppler signal at predetermined times within a narrow window of time. The predetermined times correspond to a signal from the center of the tube 108 and a signal about 25% or 75% into the tube 108. This may be accomplished in a single chirp event, or two sequential operations. The master oscillator 102 is used to sequence the operations of the timing generator 124 and the control and math functions chip 126. Preferably, the frequency discriminator 122 operates in an open loop mode, and the sample/hold #3 is capable of latching the output of the frequency discriminator in an 80 nsec period to provide desired spatial accuracy of the measurements.

The density and viscosity measurements are repeatedly and continuously taken while the blood sample is traveling at a substantially steady state flow condition through the tube 108. This permits the leading edge of the blood sample aspiration to be recognized in addition to any position within the blood sample aspiration that is homogenous. Thus, these measurements can also recognize partial aspiration conditions since bubbles will be detected in such a condition.

For purposes of taking the ESR and ZSR measurements, flow of the blood sample is abruptly stopped in the tube 108 and the cells begin to decelerate moving in both forward and transverse directions relative to the normal path of flow. Since the density of the blood sample has already been established as discussed above, the transmit/receive switch 104 will gate a four-cycle burst of the carrier wave of the master oscillator 102 to the sensor 106, which launches the pulse into the tube 108. In receive mode, the sensor 106 is utilized to receive the echo of the pulse, and the echo signal is processed by the bandpass filter 110 and an FM detector 128. The voltage output of the FM detector is captured by the sample/hold #2 under the control of the timing generator 124. The timing generator 124 causes the sample/hold #2 to track the output of the FM detector 128 and then, when an echo from the desired spatial position within the tube 108 is received by the sensor 106, tracking is turned off and the voltage output from the FM detector 128 is frozen by sample/hold #2. The timing for the capture position is based upon the 25% or 75% distance into the tube 108 and is corrected for proper spatial positioning by the density measurement previously determined. This timing is the same as that used for the forward Doppler sensor 118 during the previous viscosity measurements.

The forward Doppler sensor 118 operates in the ESR/ZSR measurement mode in a similar manner to its operation during a viscosity determination mode. However, only the Doppler shift at the center of the tube 108 is required to be determined by the forward Doppler sensor 118 during the ESR/ZSR measurement. Thus, sample/hold #3 is utilized to capture the signal that relates to the echo received from the center of the tube 108.

Figure 9:
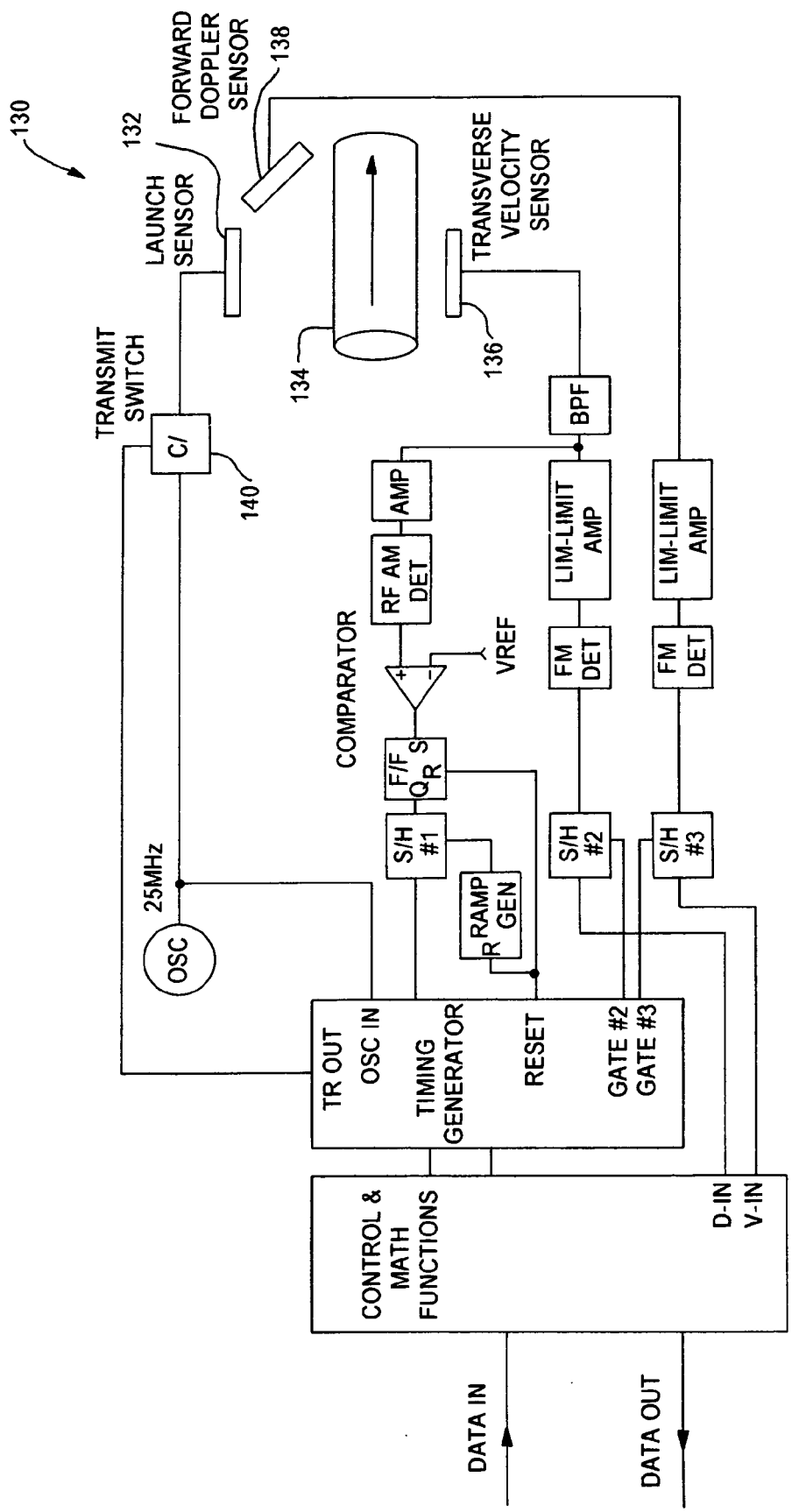
FIG. 9 is a circuit block diagram of the operations and control of a triple sensor ESR/ZSR detector according to the present invention.

An alternate three-sensor embodiment of an ESR and ZSR detector 130 is illustrated in FIG. 9. A launch sensor 132 is located adjacent to tube 134 for launching pulses, such as ultrasonic pulses, transversely across the tube 134. A transverse velocity sensor 136 is located adjacent the tube 134 opposite the launch sensor 132 for receiving signals propagating transversely through the tube 134. A forward Doppler sensor 138 is canted at an angle relative to the tube 134 for taking Doppler shift measurements of the signal as it reflects off forwardly moving cells. This embodiment functions similarly to that in FIG. 8 except that the transmit switch 140 is used only to gate the RF oscillator 142 to the launch sensor 132 and that the launch sensor 132 is not required to receive echos. Rather, the transverse velocity sensor 136 that interconnects to electronics previously described accomplishes this function.

In both of the above referenced embodiments, AM detection of the transverse signals and FM detection of the forward Doppler shift signals are sensed to determine the density and viscosity of the blood sample. AM detection is also utilized to determine the transit time of the launched pulse to determine the inside diameter of the tube as corrected for the density of the blood within the tube. The density measurement is also utilized to determine the gate timing corresponding to the central axis of the tubing and a position in the tubing about midway between the central axis and the inner diameter wall of the tubing. Viscosity of the sample is calculated from the two spatial blood velocities when the fluid is in a steady state flow condition. The density and viscosity data are subsequently used to set the gate timing for capturing the velocities of cells at known spatial positions within the tube after the fluid column is abruptly stopped. The rate of decay of the forward and transverse cell velocities provide the ESR and VSR measurements.

Although a significant number of the electronic components disclosed for the above referenced embodiments are primarily analog, other contemplated alternate embodiments of signal processors utilize electronic components that rely more heavily on digital signal processing. Thus, other electronic components and techniques for processing the Doppler shift measurements can be utilized, for example, FFT. In addition, the number of sensors can be increased or reduced and can be combined as a single multiplexed sensor or provided as separate sensors.

The ESR value is the accelerated rate of change of the deceleration of the forward motion of the cells in the sample. This value is readily determined from the information obtained by the detector, 100 or 130, discussed above. The blood sample is not required to be preheated since correction for the density and viscosity of the blood sample is applied to the data and compensates for sample temperature and overall viscosity.

The ZSR value is the accelerated rate of change of the deceleration of the transverse motion of the cells in the sample. This value is readily determined from the information obtained by the detector, 100 or 130, discussed above. The blood sample is not required to be preheated since correction for the density and viscosity of the blood sample is applied to the data and compensates for sample temperature and overall viscosity. Unlike prior art techniques, the detector and method according to the present invention evaluates the movement of cells directly to determine the ZSR value. Thus, cell movement induced by zeta potential can be measured by observing the movement of cells transversely from a starting central concentrated position within a static column of blood.

Simultaneous measurement of ESR and ZSR according to the present invention provides many advantages relative to prior art techniques. An ESR measurement traditionally requires an additional interpretation relative to the use of different scales based on the sex, age and pregnant status of the patient. However, since ESR and ZSR are measured simultaneously according to the present invention, the gender and age of the patient can be determined and reported with the values. Thus, the results of the ESR measurement does not require an additional interpretation relative to the sex, age and pregnant status of the patient; rather, this is taken into account by the detector 100 or 130. In addition, the ZSR measurement can be utilized to correct ESR values for anemic patients that would otherwise be distorted due to the low blood cell count of the patient.

Unlike prior art ESR measurement instruments, calibration of the ESR and ZSR detector according to the present invention is relatively simple since the obtained velocity data is a function of Doppler shift. One calibration alternative is to utilize standard Latron latex beads, or other weighted or iron-filled plastic beads, suspended in an isotonic fluid to provide a reference to which the detectors can be calibrated. During a steady state flow condition, the beads will become concentrated along the central axis of the tube, and when brought to an abrupt stop, will continue moving in both forward and transverse directions similar to the movements of blood cells. The latex beads carry an electrostatic charge that is induced when drawn through a capillary tube and that will repel other beads when the fluid column is brought to an abrupt stop. Alternatively, the sensors and other electronics can be calibrated and tested electronically, for instance, by transmitting selected test signals into the sensors.

Therefore, the above referenced detector and method can be utilized to simultaneously determining the density, velocity, viscosity, and ESR and ZSR values of a fluid within a tube of a blood analyzing instrument. The detector and method can also recognize the presence of bubbles in a blood sample aspiration, detect the leading and trailing edges of the blood aspiration, and determine where the sample is homogenous. The detector is self-calibrating and self-correcting for changes in tube dimensional variations and does not require a break in the tubing that leads from an aspiration needle to a destination downstream of the detector. The ESR and ZSR measurements are corrected to blood viscosity and cell density and the ESR measurement can be corrected for anemia. In addition, with the foreknowledge of the sample viscosity while aspirating, a hematology instrument can operate with variable dilutions to optimize sample processing times, for instance, of cell counting and white/red cell separation processes, and to reduce clogging events.

Multifunctional Hematology Instruments and the Like

FIG. 1 schematically illustrates a portion of hematology instrument that has an aspiration needle, or syringe, 12 to draw a blood sample by vacuum from a closed vial (not shown). The sample is passed through a first detector 14 to a blood sampling valve 16 and then through a second detector 18 before being passed onto other blood analysis sections (not shown) of the multifunctional hematology instrument 10. Detector 14 can be utilized to determine the fluid type of the sample, the density and viscosity of the blood sample, and after the blood is brought to an abrupt stop, the ESR and ZSR of the blood sample. Detector 14 can operate as previously discussed in detail with respect to detectors 20, 60, 100 and 130. Detector 18 can be a fluid-type detector according to the present invention. Thus, detectors 14 and 18 can determine whether blood, isotonic fluid or air is in the tube and can monitor blood transport to ensure that a viable aspiration was achieved. In addition, the detectors 14 and 18 can provide an indication when air is present in the sample column and when there is insufficient blood volume (ie., a partial aspiration condition). If not all of the advantages of the present invention are desired, detector 14 can be provided as just a fluid-type detector or as just a viscosity detector.

A suck-and-spit instrument is schematically illustrated in FIG. 10 in which a hematology instrument 150 has an aspiration needle, or syringe, 151 to draw a blood sample by a syringe, or displacement pump, 154 from a closed vial (not shown). The aspiration needle 151 is inserted into the closed vial from which the sample is drawn, and the sample is transported by action of the syringe, or displacement pump, 154 through a detector 152 and into a length of tubing, or reservoir line, 153. The draw is stopped after a desired volume of sample has been withdrawn from the closed vial. Thereafter, the aspiration needle 151 is withdrawn from the closed vial and moved to allow the sample, or a portion of the sample, to be dispensed into a receptacle, or receptacles. In addition, the direction of flow caused, for instance, by the displacement pump 154 can be reversed so that a desired volume of the sample can be dispensed to other blood analysis sections (not shown) of the multifunctional hematology instrument 150.

The detector 152 can be utilized to determine the fluid type of the sample, the density and viscosity of the blood sample, and after the blood is brought to an abrupt stop, the ESR and ZSR of the blood sample. Detector 152 can operate as previously discussed in detail with respect to detectors 20, 60, 100 and 130. Thus, detector 152 can determine whether blood, isotonic fluid or air is in the tube and can monitor blood transport to ensure that a viable aspiration was achieved. In addition, the detector 152 can provide an indication when air is present in the sample column and when there is insufficient blood volume (ie., a partial aspiration condition). If not all of the advantages of the present invention are desired, detector 14 can be provided as just a fluid-type detector or as just a viscosity detector.

Another example of an instrument according to the present invention is an automated slide making apparatus (not shown) that utilizes a viscosity detector according to the present invention. The disclosures of a blood-smearing member and an automated slide making apparatus in U.S. Pat. Nos. 5,650,332 and 5,804,145 issued to Gao et al. are incorporated herein by reference. The viscosity detector, such as the detector 60 illustrated in FIG. 4, can be integrated into the slide making apparatus, or be provided as a separate instrument utilized in combination with the slide making apparatus. The viscosity measurement of the detector controls the movement of a blood-smearing member, such as a smear-forming wedge (not shown), of the slidemaker. The blood smear slide can be produced immediately after the viscosity measurement is taken so that an optimal blood smear slide is produced.

With respect to all of the detectors, instruments and methods of the present invention, the fluid sample flow through the capillary tube is laminar and has a simple Gaussian cross-section velocity profile. Thus, unlike blood flow in vivo that is spiral in nature due to the non-straight nature of veins and arteries, the fluid sample flow of the present invention is along a substantially straight capillary tube. If the tube is bent at about a right angle, vortices will form and blood flow will take on spiral directionality. The distance at which a flow along a straight tube becomes purely Gaussian is a function of the velocity of the fluid and the internal diameter of the tube. For purposes of the hematology instruments of the present invention, this distance is between about 2 to 5 inches. Thus, the detectors according to the present invention should be engaged about a portion of a tube that extends along a substantially straight path for at least about five inches before the tube enters the detector. In addition, optimum placement of the sensor assembly should be as far away from the aspiration point as possible to ensure laminar flow conditions.

Blood clots are another problem that the detectors, instruments and methods of the present invention address. Blood drawn from a patient may contain blood clots as a result of induced trauma from drawing the blood or as a result of an abnormally high platelet count that begins clotting the blood before the $K_3$ETDA in the sample tube can neutralize their action. Blood that is drawn through too thin of a needle at too fast a rate will also initiate platelet activation and clumping will occur. Clumping can also be initiated at a later time if the aspiration capillary line is too small or if the sample is drawn too fast. Such blood clots and clumping have traditionally caused problems with respect to their presence in blood analyzing instruments.

The detectors of the present invention can detect the presence of blood clots and can determine the size of clots. The cross-section profile of an echo signal from a blood clot is recognizable by the detectors of the present invention since the profile is different than that from cells due to the larger size of blood clots. In addition, the chirp velocity reflecting off a blood clot is much higher than that reflecting from an air bubble, and thus an echo from a blood clot can be distinguished from that of an air bubble. In addition, the void in receiving single blood cell reflections can be measured and utilized to determine the size of the clot. If the size of the clot is deemed too large, the sample fluid can be purged from the instrument before an attempt is made at passing the sample fluid through small apertures of the instrument, such as those used to count and classify individual blood cells. Thus, an additional feature of the detectors according to the present invention is that they can prevent instruments from becoming clogged with blood clots and can prevent the required down time and effort to restore the instrument to normal working condition.

Although this invention has been described with reference to specific embodiments thereof and methods thereof, those skilled in the art will be able to develop equivalent versions of the methods for determining fluid-type, density, velocity, viscosity, ESR and ZSR of a fluid sample and to construct analogous forms of the apparatus, detectors and instruments of this invention. All such variations come within the spirit of the invention as defined in the appended claims.

The invention claimed is:

1. A device for analyzing a blood sample, comprising:
    a capillary tube defining a path of travel for flow of a blood sample in vitro; and
    a sensor assembly located about said capillary tube and having a launch sensor for emitting an ultrasound pulse into said capillary tube in a direction perpendicular to said path of travel, and
    a second sensor located forward along said path of travel relative to said launch sensor and canted at an angle relative to said path of travel so that said second sensor is aligned to receive echo signals of said ultrasound pulse that reflect off cells moving forward within said path of travel, wherein said device is adapted for measuring erythrocyte sedimentation rate (ESR) or zeta sedimentation rate (ZSR) of a blood sample.

2. A device according to claim 1, wherein said launch sensor is a piezo crystal transducer.

3. A device according to claim 1, wherein said capillary tube defines a straight path of travel adjacent said sensor assembly.

4. The device according to claim 1, wherein said launch sensor emits said ultrasound pulse in a direction perpendicular to said path of travel and along a diameter of said capillary tube.

5. The device according to claim 4, wherein a single launch sensor is utilized to emit said ultrasound pulse and receive an echo signal of said ultrasound pulse that propagates into said capillary tube in a direction away from said launch sensor and perpendicular to said path of travel and that is reflected back toward said launch sensor.

6. The device according to claim 1, further comprising:
said sensor assembly having at least one sensor for emitting a waveform pulse at a predetermined frequency into said capillary tube perpendicularly across said path of travel and for receiving at least one of said pulse and an echo of said pulse after said pulse propagates at least partially through said capillary tube and said path of travel; and
a signal processing circuit in communication with said sensor assembly.

7. The device according to claim 6, wherein, when air alone is located in said capillary tube, said signal processing circuit is adapted to determine wall thickness and inner diameter of said capillary tube based on echo signals received by said sensor assembly.

8. The device according to claim 1, further comprising a signal processing circuit interconnected to said second sensor and adapted to measure Doppler shift of echo signals received by said second sensor whereby cell velocity of the cells moving forward along said path of travel can be determined.

9. The device according to claim 8, wherein said signal processing circuit is adapted to capture Doppler shift measurements from echo signals received by said second sensor reflecting from cells located at two or more different spatial locations within said capillary tube so that a curve of velocity of cells across a cross section of said capillary tube can be generated.

10. The device according to claim 9, wherein said two or more spatial locations include locations along a central longitudinal axis of said capillary tube and about midway between said central longitudinal axis and an inner diameter wall of said capillary tube.

11. The device according to claim 1, further comprising means for abruptly halting the flow of the blood sample through said capillary tube.

12. The device according to claim 11, further comprising a signal processing circuit which interconnects to said second sensor and which is adapted to take Doppler shift measurements of echo signals received by said second sensor after flow of the blood sample in said capillary tube is caused to be abruptly halted by said means, said Doppler shift measurements are from echo signals received by said second sensor from a reflection of said ultrasound pulse off cells moving forward along said path of travel.

13. The device according to claim 12, wherein said signal processing circuit is adapted to capture Doppler shift measurements from echo signals corresponding to those received by said second sensor reflecting from cells located along a central longitudinal axis of said capillary tube.

14. The device according to claim 12, wherein said signal processing circuit interconnects to said launch sensor and is adapted to take Doppler shift measurements of echo signals received by said launch sensor after flow of the blood sample in said capillary tube is caused to be abruptly halted by said means, said Doppler shift measurements are from echo signals received by said launch sensor from a reflection of said ultrasound pulse off cells moving transversely relative to said path of travel.

15. The device according to claim 11, further comprising a signal processing circuit which interconnects to said launch sensor and which is adapted to take Doppler shift measurements of echo signals received by said launch sensor after flow of the blood sample in said capillary tube is caused to be abruptly halted by said means, said Doppler shift measurements are from echo signals received by said launch sensor from a reflection of said ultrasound pulse off cells moving transversely relative to said path of travel.

16. The device according to claim 15, wherein said signal processing circuit is adapted to capture Doppler shift measurements from echo signals corresponding to those received by said launch sensor reflecting from cells located about midway between said central longitudinal axis and an inner diameter wall of said capillary tube.

17. The device according to claim 1, wherein said sensor assembly comprises a separate receiving sensor engaging said capillary tube opposite said launch sensor utilized to receive said ultrasound pulse that propagates completely through said capillary tube and path of travel.

18. The device according to claim 1, further comprising:
a separate receiving sensor engaging said capillary tube opposite said launch sensor for receiving at least one of said pulse and an echo of said pulse after said pulse propagates completely through said capillary tube and said path of travel.

19. The device according to claim 1, wherein said capillary tube is made of a material selected from the group consisting of polyurethane and a material having a relatively low density similar to polyurethane.

20. The device according to claim 1, wherein said capillary tube further comprises a housing that encloses said sensor assembly about said capillary tube, said housing being made of a material which is of a higher density than that of said capillary tube so that said ultrasound pulse reflects off said housing.

21. The device according to claim 1, wherein said device forms a part of a multifunctional hematology instrument having a blood aspiration drawing mechanism interconnected to said capillary tube at an upstream location relative to said sensor assembly.

22. The device according to claim 1, wherein said device forms a part of an automated blood smear slide maker having a wedge component for producing a monolayer smear of cells, and wherein at least one of hold time, smear velocity and acceleration of said wedge component is determined as a function of flight time and Doppler shift measurements taken by said sensor assembly.

23. The device according to claim 1, further comprising a signal processor in communication with said at least one sensor for measuring at least one of flight time of the received pulse/echo and Doppler shift of said echo.

24. A method for analyzing a fluid sample, comprising:
flowing a blood sample in vitro in a path of travel within a capillary tube of the device of claim 1;
emitting a waveform pulse of a predetermined frequency into said capillary tube and perpendicularly into said path of travel;
receiving said pulse by a sensor after said pulse propagates at least partially though said capillary tube and said path of travel; and
measuring at least one of flight time and Doppler shift of said pulse received during said receiving step and determining at least one of ESR and ZSR therefrom.

25. The method according to claim 24, wherein the pulse is an ultrasound pulse.

26. The method according to claim 25, wherein the ultrasound pulse emitted during said emitting step is directed substantially perpendicular to the path of travel of the blood sample and along a diameter of the capillary tube.

27. The method according to claim 26, wherein, during said receiving step, an ultrasound pulse is received after it has propagated at least once completely through the capillary tube and path of travel, and during the measuring step, the flight time of the ultrasound pulse that propagated at least once through the capillary tube and path of travel is determined and utilized to determine the density of the fluid sample.

28. The method according to claim 27, further comprising the step of monitoring the presence or lack thereof of noise reflections of the ultrasound pulse off particles in the fluid sample to distinguish between isotonic fluids and blood.

29. The method according to claim 28, further comprising the step of reporting the presence of air, isotonic fluids or blood within the capillary tube based on information obtained during said measuring and monitoring steps.

30. The method according to claim 26, wherein, during said receiving step, echo signals from the ultrasound pulse reflecting off cells moving forward within the capillary tube are received, and during the measuring step, the Doppler shift of the echo signals is measured to determine the velocity of the blood sample, whereby the velocity measurement of the blood sample combined with information concerning the density of the blood sample is utilized to determine the viscosity of the blood sample.

31. The method according to claim 30, wherein during said measuring step, Doppler shift measurements are taken from echo signals which reflect from cells located at least at two different spatial locations within a cross-section of the capillary tube, and wherein a profile curve of blood velocity across the cross section of the capillary tube is generated.

32. The method according to claim 31, wherein the spatial locations include locations along a central longitudinal axis of the capillary tube and about midway between the central longitudinal axis and an inner diameter wall of the capillary tube.

33. A method for analyzing a fluid sample comprising:
flowing a blood sample in vitro in a path of travel within a capillary tube;
emitting a waveform ultrasound pulse of a predetermined frequency in direction directed transversely across the path of travel of the blood sample;
receiving said pulse by a sensor after said pulse propagates at least partially through said capillary tube and said path of travel;
stopping the flow of the blood sample in an abrupt manner within the capillary tube;
wherein said emitting step is accomplished after the flow of the blood sample is abruptly stopped;
wherein, during said receiving step, echo signals are simultaneously received from the ultrasound pulse reflecting off cells moving forward relative to the path of travel within the capillary tube and off cells moving transversely relative to a central longitudinal axis of the capillary tube after the flow of the blood sample is abruptly stopped; and
wherein, during said measuring step, the Doppler shift of the echo signals are measured to determine the rate of decay of velocity of forward moving cells and the rate of decay of velocity of cells moving in a transverse direction;
whereby the measured rate of decay of the velocity of forward moving cells is utilized to determine an ESR value for the blood sample and the rate of decay of velocity of the cells moving transversely is utilized to determine a ZSR value for the blood sample.

34. The method according to 33, wherein during said measuring step, Doppler shift measurements for determining the rate of decay of velocity of forward moving cells are obtained from echo signals which reflect from cells located along the central longitudinal axis of the capillary tube.

35. The method according to claim 34, wherein during said measuring step, Doppler shift measurements for determining the rate of decay of velocity of cells moving in a transverse direction is taken from echo signals which reflect from cells located about midway between the central longitudinal axis and an inner diameter wall of the capillary tube.

* * * * *